United States Patent
Linker et al.

(10) Patent No.: US 6,551,963 B1
(45) Date of Patent: *Apr. 22, 2003

(54) PHENYLPYRIDAZINONES

(75) Inventors: Karl-Heinz Linker, Leverkusen (DE); Kurt Findeisen, Leverkusen (DE); Wilhelm Haas, Pulheim (DE); Markus Dollinger, Leverkusen (DE); Hans-Joachim Santel, Leverkusen (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/952,817

(22) PCT Filed: May 24, 1996

(86) PCT No.: PCT/EP96/02246
§ 371 (c)(1),
(2), (4) Date: Nov. 26, 1997

(87) PCT Pub. No.: WO96/39392
PCT Pub. Date: Dec. 12, 1996

(30) Foreign Application Priority Data

Jun. 6, 1995 (DE) .......... 195 20 613

(51) Int. Cl.$^7$ .................. A01N 43/58; C07D 237/06
(52) U.S. Cl. ............. 504/238; 544/239; 544/240; 544/241
(58) Field of Search ............. 504/238; 544/239, 544/240, 241

(56) References Cited

U.S. PATENT DOCUMENTS

| | | | |
|---|---|---|---|
| 5,298,502 A | * 3/1994 | Halling et al. | 514/185 |
| 6,022,829 A | 2/2000 | Mito | 504/134 |
| 6,040,270 A | 3/2000 | Mito | 504/128 |
| 6,077,953 A | 6/2000 | Kawamura | 544/239 |
| 6,090,753 A | * 7/2000 | Katayama et al. | 504/238 |
| 6,093,818 A | * 7/2000 | Furukawa | 544/239 |
| 6,107,250 A | 8/2000 | Tohyama et al. | 504/238 |
| 6,121,194 A | 9/2000 | Mito | 504/134 |
| 6,147,030 A | 11/2000 | Mito | 504/132 |
| 6,197,727 B1 | * 3/2001 | Hoshi | 504/134 |
| 6,211,118 B1 | * 4/2001 | Hoshi | 504/134 |
| 6,218,338 B1 | 4/2001 | Mito | 504/134 |
| 6,225,313 B1 | * 5/2001 | Schafer et al. | 514/247 |
| 6,355,799 B1 | 3/2002 | Gupta et al. | 544/309 |
| 2002/0045550 A1 | 4/2002 | Carlsen et al. | 504/242 |

FOREIGN PATENT DOCUMENTS

| | | |
|---|---|---|
| CH | 373 919 | 1/1964 |
| DE | 950 287 | 10/1956 |
| EP | 0 003 805 | 9/1979 |
| EP | 0 210 647 | 2/1987 |
| EP | 0 224 094 | 6/1987 |
| FR | 2 381 033 | 9/1978 |

OTHER PUBLICATIONS

"Heilmittelchemische Studien in der heterocyclischen Reihe," Druey, et al., Helvetica Chimica Acta, vol. XXXVII, Fasciculus II (1954), No. 62, pp. 510–521 (in German with English translation).

"Maleinaldehyd– und Fumaraldehydsäure," von Siegfried, et al., Bd. 697 (1966), pp. 42–54 (in German with English translation.

English translation of German Patent 950 287 (Oct. 4, 1956).
English translation of Swiss Patent 373 919 (Jan. 31, 1964).

* cited by examiner

*Primary Examiner*—Brenda Coleman
(74) *Attorney, Agent, or Firm*—Norris McLaughlin & Marcus

(57) ABSTRACT

The invention relates to novel phenylpyridazinones of the general formula (I)

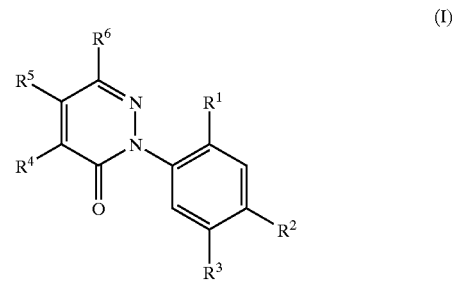

in which $R^1$, $R^2$, $R^3$, $R^4$, $R^5$ and $R^6$ are each as defined in the description, to processes for their preparation, to their use as herbicides and to novel intermediates and processes for preparing them.

11 Claims, No Drawings

PHENYLPYRIDAZINONES

This application is a 371 of PCT/EP96/02246, which was filed on May 24, 1996.

The invention relates to novel phenylpyridazinones, to processes for their preparation, to their use as herbicides and to novel intermediates and to processes for their preparation.

It is known that certain substituted phenylpyridazinones such as, for example, the compounds 5-amino-4-chloro-2-phenyl-pyridazin-3-one and 4-bromo-5-methyl-2-phenyl-pyridazin-3-one have herbicidal properties (cf. DE 1105232 and DE 2706700; cf. also DE 1670309, DE 1670315, DE 1695840, DE 2526643, DE 2808193, DE 2821809 and U.S. Pat. No. 5,298,502). However, the herbicidal activity of these compounds is not in all respects satisfactory.

This invention, accordingly, provides the novel substituted phenylpyridazinones of the general formula (I)

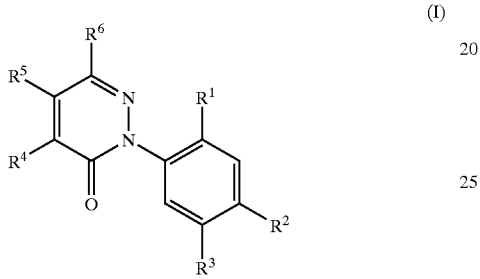

(I)

in which
- $R^1$ represents halogen,
- $R^2$ represents cyano, carbamoyl, thiocarbamoyl, halogen or represents respectively optionally halogen-substituted alkyl, alkoxy or alkylthio,
- $R^3$ represents the grouping —$A^1$—$A^2$—$A^3$
  in which
  - $A^1$ represents a single bond, represents oxygen, sulphur, —SO—, —$SO_2$—, —CO— or the grouping —N—$A^4$— where $A^4$ represents hydrogen, hydroxyl, alkyl, alkenyl, alkinyl, alkoxy, aryl, alkyl-sulphonyl or aryl-sulphonyl,
  - $A^1$ furthermore represents respectively optionally halogen-substituted alkanediyl, alkenediyl, azaalkenediyl, alkinediyl, cycloalkanediyl, cycloalkenediyl or phenylene,
  - $A^2$ represents a single bond, represents oxygen, sulphur, —SO—, —$SO_2$—, —CO— or the grouping —N—$A^4$— where $A^4$ represents hydrogen, hydroxyl, alkyl, alkoxy, aryl, alkylsulphonyl or arylsulphonyl,
  - $A^2$ furthermore represents respectively optionally halogen-substituted alkanediyl, alkenediyl, azaalkenediyl, alkinediyl, cycloalkanediyl, cycloalkenediyl or phenylene,
  - $A^3$ represents hydrogen with the proviso that in this case $A^1$ and/or $A^2$ do not represent a single bond,
  - $A^3$ furthermore represents hydroxyl, amino, cyano, isocyano, thiocyanato, nitro, carboxy, carbamoyl, thiocarbamoyl, sulpho, chlorosulphonyl, halogen,
  - $A^3$ furthermore represents respectively optionally halogen- or alkoxy-substituted alkyl, alkoxy, alkylthio, alkylsulphinyl, alkylsulphonyl, alkylamino, dialkylamino, alkoxycarbonyl or dialkoxy(thio)phosphoryl,
  - $A^3$ furthermore represents respectively optionally halogen-substituted alkenyl, alkenyloxy, alkenylamino, alkylideneamino, alkenyloxycarbonyl, alkinyl, alkinyloxy, alkinylamino or alkinyloxycarbonyl, represents respectively optionally halogen-, cyano-, carboxy-, alkyl- and/or alkoxy-carbonyl-substituted cycloalkyl, cycloalkyloxy, cycloalkylalkyl, cycloalkylalkoxy, cycloalkylideneamino, cycloalkyloxycarbonyl or cycloalkylalkoxycarbonyl,
  - $A^3$ furthermore represents respectively optionally nitro-, cyano-, carboxy-, halogen-, alkyl-, halogenoalkyl-, alkyloxy-, halogenoalkyloxy- and/or alkoxy-carbonyl-substituted aryl, aryloxy, aralkyl, arylalkoxy, aryloxycarbonyl or arylalkoxycarbonyl,
  - $A^3$ furthermore represents respectively optionally fully or partially hydrogenated pyrrolyl, pyrazolyl, imidazolyl, triazolyl, furyl, oxiranyl, oxetanyl, dioxolanyl, thienyl, oxazolyl, isoxazolyl, thiazolyl, isothiazolyl, oxadiazolyl, thiadiazolyl, pyridinyl, pyrimidinyl, triazinyl, pyrazolylalkyl, furylalkyl, thienylalkyl, oxazolylalkyl, isoxazolalkyl, thiazolalkyl, pyridinylalkyl, pyrimidinylalkyl, pyrazolylalkoxy, furylalkoxy, perhydropyranylalkoxy or pyridylalkoxy, or
- $R^2$ and $R^3$ together represent one of the groupings below —$Q^1$—$CQ^2$—, —$Q^1$—$CQ^2$—$Q^3$—, —$Q^1$—$C(R^7,R^8)$—$Q^3$—, —$C(R^7,R^8)$—$CQ^2$—, —$C(R^7,R^8)$—$Q^1$—$CQ^2$—, —$Q^1$—$C(R^7,R^8)$—$C(R^7,R^8)$—, —$Q^1$—$C(R^7,R^8)$—$C(R^7,R^8)$—$Q^3$—, —$C(R^7,R^8)$—$C(R^7,R^8)$—$CQ^2$—, —$Q^1$—$C(R^7)$=$C(R^7)$—, —$C(R^7)$=$C(R^7)$—$CQ^2$—, —$Q^1$—$C(R^7,R^8)$—$CQ^2$—, —$N(R^9)$—$C(R^7;R^8)$—$CQ^2$—, —$C(R^7)$=$N$—, —$Q^1$—$CQ^2$—$C(R^7,R^8)$—, —$Q^1$—$CQ^2$—$N(R^9)$—, —$Q^1$—$C(R^7,R^8)$—$CQ^2$—$N(R^9)$—, —$C(R^7,R^8)$—$Q^1$—$CQ^2$—$N(R^9)$—, —$C(R^7,R^8)$—$C(R^7,R^8)$—$C(R^7,R^8)$—$N(R^9)$—, —$C(R^7,R^8)$—$C(R^7,R^8)$—$CQ^2$—$N(R^9)$—, —$C(R^7)$=$C(R^7)$—$N(R^9)$—, —$C(R^7)$=$C(R^7)$—$CQ^2$—$N(R^9)$—, —$C(R^7,R^8)$—$CQ^2$—$N(R^9)$—, —$N(R^9)$—$C(R^7;R^8)$—$CQ^2$—$N(R^9)$—, —$C(R^7)$=$N$—$N(R^9)$—, —$Q^1$—$CQ^2$—$C(R^7,R^8)$—$N(R^9)$—, $Q^1$—$C(R^7,R^8)$—$C(R^7,R^8)$—$CQ^2$—$N(R^9)$—
  where
  - $Q^1$, $Q^2$ and $Q^3$ are identical or different and each represents oxygen or sulphur,
  - $R^7$ and $R^8$ are identical or different and each on its own represents hydrogen, halogen or alkyl, or together they represent alkanediyl, and
  - $R^9$ represents hydrogen, hydroxyl, represents optionally cyano-, halogen-, alkoxy-, alkyl-carbonyl- or alkoxy-carbonyl-substituted alkyl, alkylcarbonyl, alkoxycarbonyl or alkylsulphonyl,
  - $R^9$ furthermore represents respectively optionally halogen-substituted alkenyl or alkinyl,
  - $R^9$ furthermore represents respectively optionally halogen- or alkyl-substituted cycloalkyl or cycloalkylalkyl, represents respectively optionally halogen-substituted alkoxy or alkenyloxy, or
  - $R^9$ furthermore represents respectively optionally cyano-, halogen- alkyl-, halogenoalkyl-, alkoxy- or halogenoalkoxy-substituted arylalkyl or arylalkoxy, and
- $R^4$, $R^5$ and $R^6$ are identical or different and each represents hydrogen, cyano, thiocarbamoyl, nitro, hydroxyl, mercapto, amino, halogen or represents respectively optionally halogen-substituted alkyl, alkoxy, alkylthio, alkylamino or dialkylamino,
except for the prior art compounds 2-(2,4,5-trichloro-phenyl)-pyridazin-3-one (cf. Liebigs. Ann. Chem. 697

(1966), 42–61) and 4-chloro-5-dimethylamino-2-(4-chloro-2-fluoro-5-propargyloxy-phenyl)-pyridazin-3-one (cf. U.S. Pat No. 5,298,502), which are excluded by disclaimer.

The novel substituted phenylpyridazinones of the general formula (I) are obtained when (a) halogenoarenes of the general formula (II)

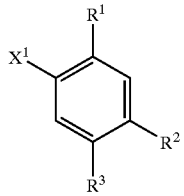

(II)

in which
R$^1$, R$^2$ and R$^3$ are each as defined above and
X$^1$ represents halogen
are reacted with pyridazinones of the general formula (III)

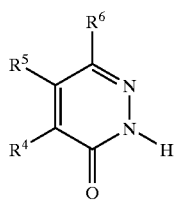

(III)

in which
R$^4$, R$^5$ and R$^6$ are each as defined above—or with acid adducts or alkali metal salts of compounds of the formula (III)—if appropriate in the presence of a reaction auxiliary and if appropriate in the presence of a diluent, or (b) aryihydrazines of the general formula (IV)

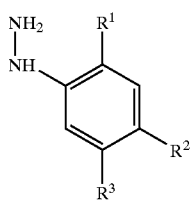

(IV)

in which
R$^1$, R$^2$ and R$^3$ are each as defined above are reacted with β-trihalomethyl-enones of the general formula (V)

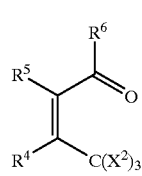

(V)

in which
R$^4$, R$^5$ and R$^6$ are each as defined above and
X$^2$ represents halogen,
if appropriate in the presence of a reaction auxiliary and if appropriate in the presence of a diluent, or (c) hydrazonecarboxylic acids of the general formula (VI)

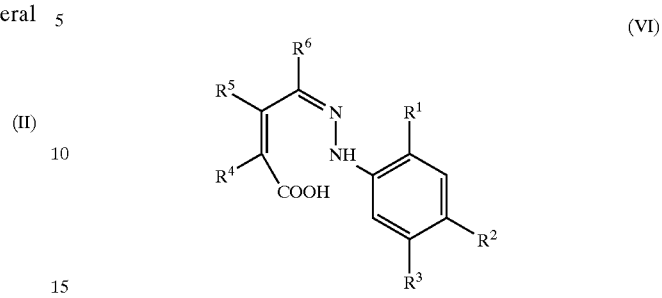

(VI)

in which
R$^1$, R$^2$, R$^3$, R$^4$, R$^5$ and R$^6$ are each as defined above are cyclocondensed, i.e. reacted with a dehydrating agent, or (d) 2,4-disubstituted phenylpyridazinones of the general formula (Ia)

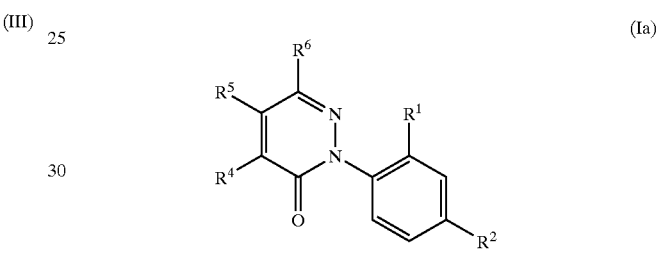

(Ia)

in which
R$^1$, R$^2$, R$^4$, R$^5$ and R$^6$ are each as defined above are nitrated, i.e. reacted with a nitrating agent.

The compounds of the general formula (I) can also be converted into other compounds of the general formula (I) according to the definition above by further customary methods, for example by nucleophilic substitution (for example R$^3$: F→OH, SH, NH$_2$, OCH$_3$, NHSO$_2$CH$_3$; R5: Cl→N(CH$_3$)$_2$) or by further functional group conversions (for example R$^2$: CONH$_2$→CN, CN→CSNH$_2$; R$^3$: NO$_2$→NH$_2$, NH$_2$→F, Cl, Br, CN, NHSO$_2$CH$_3$, SO$_2$Cl)—cf. also the Preparation Examples.

The novel substituted phenylpyridazinones of the general formula (I) have strong herbicidal activity.

In the definitions, the saturated or unsaturated hydrocarbon chains, such as alkyl, alkenyl or alkinyl, are in each case straight-chain or branched.

Halogen generally represents fluorine, chlorine, bromine or iodine, preferably fluorine, chlorine or bromine, in particular fluorine or chlorine.

The invention preferably provides compounds of the formula (I) in which

R$^1$ represents fluorine, chlorine or bromine,

R$^2$ represents cyano, carbamoyl, thiocarbamoyl, fluorine, chlorine, bromine, or represents respectively optionally fluorine- and/or chlorine-substituted alkyl, alkoxy or alkylthio having in each case 1 or 2 carbon atoms, R$^3$ represents the grouping —A$^1$—A$^2$—A$^3$
in which
A$^1$ represents a single bond, represents oxygen, sulphur, —SO—, —SO$_2$—, —CO— or the grouping —N—A$^4$— in which A$^4$ represents hydrogen, hydroxyl, $C_1$–$C_4$-alkyl, $C_3$–$C_4$-alkenyl, $C_3$–$C_4$-alkinyl, $C_1$–$C_4$-alkoxy, phenyl, $C_1$–$C_4$-alkylsulphonyl or phenylsulphonyl, $A^1$ furthermore represents respectively optionally fluorine-, chlorine- or bromine-substituted $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene, $A^2$ represents a single bond, represents oxygen, sulphur, —SO—, —$SO_2$—, —CO— or the grouping —N—$A^4$— in which $A^4$ represents hydrogen, hydroxyl, $C_1$–$C_4$-alkyl, $C_1$–$C_4$-alkoxy, phenyl, $C_1$–$C_4$-alkylsulphonyl or phenylsulphonyl, $A^2$ furthermore represents respectively optionally fluorine-, chlorine- or bromine-substituted $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene, $A^3$ represents hydrogen, with the proviso that in this case $A^1$ and/or $A^2$ do not represent a single bond, $A^3$ furthermore represents hydroxyl, amino, cyano, isocyano, thiocyanato, nitro, carboxy, carbamoyl, thiocarbamoyl, sulpho, chlorosulphonyl, fluorine, chlorine, bromine, $A^3$ furthermore represents respectively optionally fluorine-, chlorine- or $C_1$–$C_4$-alkoxy-substituted alkyl, alkoxy, alkylthio, alkylsulphinyl, alkylsulphonyl, alkylamino, dialkylamino, alkoxycarbonyl or dialkoxy(thio)phosphoryl having in each case 1 to 6 carbon atoms in the alkyl groups, $A^3$ furthermore represents respectively optionally fluorine- or chlorine-substituted alkenyl, alkenyloxy, alkenylamino, alkylideneamino, alkenyloxycarbonyl, alkinyl, alkinyloxy, alkinylamino or alkinyloxycarbonyl having in each case 2 to 6 carbon atoms in the alkenyl, alkylidene or alkinyl groups, $A^3$ furthermore represents respectively optionally fluorine-, chlorine- cyano-, carboxy-, $C_1$–$C_4$-alkyl- and/or $C_1$–$C_4$-alkoxy-carbonyl-substituted cycloalkyl, cycloalkyloxy, cycloalkylalkyl, cycloalkylalkoxy, cycloalkylideneamino, cycloalkyloxycarbonyl or cycloalkylalkoxycarbonyl having in each case 3 to 6 carbon atoms in the cycloalkyl groups and optionally 1 to 4 carbon atoms in the alkyl groups, $A^3$ furthermore represents respectively optionally nitro-, cyano-, carboxy-, fluorine-, chlorine-, bromine-, $C_1$–$C_4$-alkyl-, $C_1$–$C_4$-halogenoalkyl-, $C_1$–$C_4$-alkyloxy-, $C_1$–$C_4$-halogenoalkyloxy- and/or $C_1$–$C_4$-alkoxy-carbonyl-substituted phenyl, phenyloxy, phenyl-$C_1$–$C_4$-alkyl, phenyl-$C_1$–$C_4$-alkoxy, phenyloxycarbonyl or phenyl-$C_1$–$C_4$-alkoxycarbonyl, $A^3$ furthermore represents respectively optionally fully or partially hydrogenated pyrrolyl, pyrazolyl, imidazolyl, triazolyl, furyl, oxiranyl, oxetanyl, dioxolanyl, thienyl, oxazolyl, isoxazolyl, thiazolyl, isothiazolyl, oxadiazolyl, thiadiazolyl, pyridinyl, pyrimidinyl, triazinyl, pyrazolyl-$C_1$–$C_4$-alkyl, furyl-$C_1$–$C_4$-alkyl, thienyl-$C_1$–$C_4$-alkyl, oxazolyl-$C_1$–$C_4$-alkyl, isoxazol-$C_1$–$C_4$-alkyl, thiazol-$C_1$–$C_4$-alkyl, pyridinyl-$C_1$–$C_4$-alkyl, pyrimidinyl-$C_1$–$C_4$-alkyl, pyrazolylmethoxy, furylmethoxy, represents perhydropyranylmethoxy or pyridylmethoxy, or $R^2$ and $R^3$ together represent one of the groupings below —$Q^1$—$CQ^2$—, —$Q^1$—$CQ^2$—$Q^3$—, —$Q^1$—$C(R^7,R^8)$—$Q^3$—, —$C(R^7,R^8)$—$CQ^2$—, —$C(R^7,R^8)$—$Q^1$—$CQ^2$—, —$Q^1$—$C(R^7,R^8)$—$C(R^7,R^8)$—, —$Q^1$—$C(R^7,R^8)$—$C(R^7,R^8)$—$Q^3$—, —$C(R^7,R^8)$—$C(R^7,R^8)$—$CQ^2$—, —$Q^1$—$C(R^7)$=$C(R^7)$—, —$C(R^7)$=$C(R^7)$—$CQ^2$—, —$Q^1$—$C(R^7,R^8)$—$CQ^2$—, —$N(R^9)$—$C(R^7;R^8)$—$CQ^2$—, —$C(R^7)$=$N$—, —$Q^1$—$CQ^2$—$C(R^7,R^8)$—, —$Q^1$—$CQ^2$—$N(R^9)$—, —$Q^1$—$C(R^7,R^8)$—$CQ^2$—$N(R^9)$—, —$C(R^7,R^8)$—$Q^1$—$CQ^2$—$N(R^9)$—, —$C(R^7,R^8)$—$C(R^7,R^8)$—$N(R^9)$—, —$C(R^7,R^8)$—$C(R^7,R^8)$—$CQ_2$—$N(R^9)$—, —$C(R^7)$=$C(R^7)$—$N(R^9)$—, —$C(R^7)$=$C(R^7)$—$CQ^2$—$N(R^9)$—, —$C(R^7,R^8)$—$CQ^2$—$N(R^9)$—, —$N(R^9)$—$C(R^7;R^8)$—$CQ^2$—$N(R^9)$—, —$C(R^7)$=$N$—$N(R^9)$—, —$Q^1$—$CQ^2$—$C(R^7,R^8)$—$N(R^9)$—, —$Q^1$—$C(R^7,R^8)$—$C(R^7,R^8)$—$CQ^2$—$N(R^9)$— where $Q^1$, $Q^2$ and $Q^3$ are identical or different and each represents oxygen or sulphur, $R^7$ and $R^8$ are identical or different and each on its own represents hydrogen, fluorine, chlorine, bromine or $C_1$–$C_4$-alkyl, or together they represent $C_2$–$C_5$-alkanediyl, and $R^9$ represents hydrogen, hydroxyl, represents optionally cyano-, fluorine-, chlorine-, $C_1$–$C_4$-alkoxy-, $C_1$–$C_4$-alkyl-carbonyl- or $C_1$–$C_4$-alkoxy-carbonyl-substituted alkyl, alkylcarbonyl, alkoxycarbonyl or alkylsulphonyl having in each case 1 to 6 carbon atoms in the alkyl groups, $R^9$ furthermore represents respectively optionally fluorine-, chlorine- or bromine-substituted alkenyl or alkinyl having in each case 2 to 6 carbon atoms, $R^9$ furthermore represents respectively optionally fluorine-, chlorine-, bromine- or $C_1$–$C_4$-alkyl-substituted cycloalkyl or cycloalkylalkyl having in each case 3 to 6 carbon atoms in the cycloalkyl groups and optionally 1 to 3 atoms in the alkyl group, $R^9$ furthermore represents respectively optionally fluorine- and/or chlorine-substituted alkoxy or alkenyloxy having in each case up to 6 carbon atoms, or $R^9$ furthermore represents respectively optionally cyano-, fluorine-, chlorine-, $C_1$–$C_4$-alkyl-, $C_1$–$C_4$-halogenoalkyl-, $C_1$–$C_4$-alkoxy- or $C_1$–$C_4$-halogenoalkoxy-substituted benzyl or benzyloxy, and $R^4$, $R^5$ and $R^6$ are identical or different and each represents hydrogen, cyano, thiocarbamoyl, nitro, hydroxyl, mercapto, amino, fluorine, chlorine, bromine, or represents respectively optionally fluorine- and/or chlorine-substituted alkyl, alkoxy, alkylthio, alkylamino or dialkylamino having in each case 1 to 4 carbon atoms in the alkyl groups, except for the prior art compounds 2-(2,4,5-trichlorophenyl)-pyridazin-3-one (cf. Liebigs Ann. Chem. 697 (1966), 42–61) and 4-chloro-5-dimethylamino-2-(4-chloro-2-fluoro-5-propargyloxy-phenyl)-pyridazin-3-one (cf. U.S. Pat. No. 5298502), which are excluded by disclaimer.

The invention relates in particular to compounds of the formula (I) in which $R^1$ represents fluorine or chlorine, $R^2$ represents cyano, thiocarbamoyl, fluorine, chlorine, bromine, methyl or trifluoromethyl, $R^3$ represents the grouping —$A^1$—$A^2$—$A^3$ in which $A^1$ represents a single bond, represents oxygen, sulphur, —SO—, —$SO_2$—, —CO— or the grouping —N—A⁴— in which A⁴ represents hydrogen, hydroxyl, methyl, ethyl, n- or i-propyl, methoxy, ethoxy, n- or i-propoxy, methylsulphonyl or ethylsulphonyl, $A^1$ furthermore represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl, propine-1,2-diyl or propine-1,3-diyl, $A^2$ represents a single bond, represents oxygen, sulphur, —SO—, —SO₂—, —CO— or the grouping —N—A⁴— in which A⁴ represents hydrogen, hydroxyl, methyl, ethyl, n- or i-propyl, methoxy, ethoxy, n- or i-propoxy, methylsulphonyl, ethylsulphonyl, n- or i-propylsulphonyl or phenylsulphonyl, $A^2$ furthermore represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl, propine-1,2-diyl or propine-1,3-diyl, $A^3$ represents hydrogen with the proviso that in this case $A^1$ and/or $A^2$ do not represent a single bond, $A^3$ furthermore represents hydroxyl, amino, cyano, nitro, carboxy, carbamoyl, sulpho, fluorine, chlorine, bromine, $A^3$ furthermore represents respectively optionally fluorine-, chlorine-, methoxy- or ethoxy-substituted methyl, ethyl, n- or i-propyl, n-, i-, s- or t-butyl, n-, i-, s- or t-pentyl, methoxy, ethoxy, n- or i-propoxy, n-, i-, s- or t-butoxy, n-, i-, s- or t-pentyloxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, methoxycarbonyl, ethoxycarbonyl, n- or i-propoxycarbonyl, dimethoxyphosphoryl, diethoxyphosphoryl, dipropoxyphosphoryl or diisopropoxyphosphoryl, $A^3$ furthermore represents respectively optionally fluorine- or chlorine-substituted propenyl, butenyl, propenyloxy, butenyloxy, propenylamino, butenylamino, propylideneamino, butylideneamino, propenyloxycarbonyl, butenyloxycarbonyl, propinyl, butinyl, propinyloxy, butinyloxy, propinylamino, butinylamino, propinyloxycarbonyl or butinyloxycarbonyl, $A^3$ furthermore represents respectively optionally fluorine-, chlorine-, cyano-, carboxy-, methyl-, ethyl-, n- or i-propyl-, methoxycarbonyl- or ethoxycarbonyl-substituted cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopentylideneamino, cyclohexylideneamino, cyclopentyloxycarbonyl, cyclohexyloxycarbonyl, cyclopentylmethoxycarbonyl, or cyclohexylmethoxycarbonyl, $A^3$ furthermore represents respectively optionally nitro-, cyano-, carboxy-, fluorine-, chlorine-, bromine-, methyl-, ethyl, n- or i-propyl-, trifluoromethyl-, methoxy-, ethoxy-, n- or i-propoxy-, difluoromethoxy-, trifluoromethoxy-, methoxycarbonyl- and/or ethoxycarbonyl-substituted phenyl, phenyloxy, benzyl, phenylethyl, benzyloxy, phenyloxycarbonyl, benzyloxycarbonyl, $A^3$ furthermore represents (respectively optionally fully or partially hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolylmethyl, furylmethyl, thienylmethyl, oxazolylmethyl, isoxazolmethyl, thiazolmethyl, pyridinylmethyl, pyrimidinylmethyl, pyrazolylmethoxy, furylmethoxy or pyridylmethoxy, or $R^2$ and $R^3$ together represent one of the groupings below
—Q¹—CQ²—, —Q¹—CQ²—Q³—, —Q¹—C(R⁷,R⁸)—Q³—, —C(R⁷,R⁸)—CQ²—, —C(R⁷,R⁸)—Q¹—CQ²—, —Q¹—C(R⁷,R⁸)—C(R⁷,R⁸)—, —Q¹—C(R⁷,R⁸)—C(R⁷,R⁸)—Q³—, —C(R⁷,R⁸)—C(R⁷,R⁸)—CQ²—, —Q¹—C(R⁷)=C(R⁷)—, —C(R⁷)=C(R⁷)—CQ²—, —Q¹—C(R⁷,R⁸)—CQ²—, —N(R⁹)—C(R⁷;R⁸)—CQ²—, —C(R⁷)=N—, —Q¹—CQ²—C(R⁷,R⁸)—, —Q¹—CQ²—N(R⁹)—, —Q¹—C(R⁷,R⁸)—CQ²—N(R⁹)—, —C(R⁷,R⁸)—Q¹—CQ²—N(R⁹)—, —C(R⁷,R⁸)—C(R⁷,R⁸)—N(R⁹)—, —C(R⁷,R⁸)—C(R⁷,R⁸)—CQ²—N(R⁹)—, —C(R⁷)=C(R⁷)—N(R⁹)—, —C(R⁷)=C(R⁷)—CQ²—N(R⁹)—, —C(R⁷,R⁸)—CQ²—N(R⁹)—, —N(R⁹)—C(R⁷;R⁸)—CQ²—N(R⁹)—, —C(R⁷)=N—N(R⁹)—, —Q¹—CQ²—C(R⁷,R⁸)—N(R⁹)—, —Q¹—C(R⁷,R⁸)—C(R⁷,R⁸)—CQ²—N(R⁹)— where $Q^1$, $Q^2$ and $Q^3$ are identical or different and each represents oxygen or sulphur, $R^7$ and $R^8$ are identical or different and each on its own represents hydrogen, fluorine, chlorine, bromine or methyl, or together they represent ethane-1,2-diyl (dimethylene), and $R^9$ represents hydrogen, hydroxyl, represents optionally cyano-, fluorine-, chlorine-, methoxy-, ethoxy-, acetyl- propionyl-, methoxycarbonyl- or ethoxycarbonyl-substituted methyl, ethyl, n- or i-propyl, n-, i-, s- or t-butyl, $R^9$ furthermore represents respectively optionally fluorine-, chlorine- or bromine—substituted propenyl, butenyl, propinyl or butinyl, $R^9$ furthermore represents respectively optionally fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, $R^9$ furthermore represents respectively optionally fluorine- and/or chlorine-substituted methoxy, ethoxy, n- or i-propoxy, n-, i- or s-butoxy, propenyloxy or butenyloxy, or $R^9$ furthermore represents respectively optionally cyano, fluorine-, chlorine-, methyl-, ethyl-, trifluoromethyl-, methoxy-, ethoxy-, difluoromethoxy- or trifluoromethoxy-substituted benzyl or benzyloxy, and, $R^4$, $R^5$ and $R^6$ are identical or different and each represents hydrogen, cyano, thiocarbamoyl, nitro, hydroxyl, mercapto, amino, fluorine, chlorine, bromine, or represents respectively optionally fluorine- and/or chlorine-substituted methyl, ethyl, n- or i-propyl, n-, i-, s- or t-butyl, methoxy, ethoxy, methylthio, ethylthio, methylamino, ethylamino or dimethylamino, except for the prior art compounds 2-(2,4,5-trichloro-phenyl)- pyridazin-3-one (cf. Liebigs Ann. Chem. 697 (1966), 42–61) and 4-chloro-5-dimethylamino-2-(4-chloro-2-fluoro-5-propargyloxy-phenyl)-pyridazin-3-one (cf. U.S. Pat. No. 5,298,502), which are excluded by disclaimer.

The general or preferred radical definitions listed above are valid also for the end products of the formula (I) and also, correspondingly, for the starting materials or intermediates required in each case for the preparation. These radical definitions can be combined with each other at will, i.e. combinations between the preferred ranges mentioned are also possible.

Examples of the compounds of the formula (I) according to the invention are listed in the groups below.

Group 1

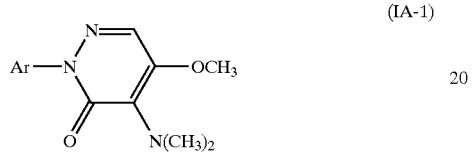
(IA-1)

Ar has for example the meanings listed below:
2,4,5-trichloro-phenyl, 2,4-dichloro-5-fluoro-phenyl, 2-chloro4,5-difluoro-phenyl, 4-chloro-2,5-difluoro-phenyl, 5-chloro-2,4-difluoro-phenyl, 2-fluoro-5-chloro-4-cyano-phenyl, 2,4,5-trifluoro-phenyl, 2,5-dichloro-4-cyano-phenyl, 2-chloro-5-fluoro-4-cyano-phenyl, 2-chloro-4,5-dicyano-phenyl, 2-chloro-4-fluoro-5-cyano-phenyl, 2,5-difluoro-4-cyano-phenyl, 2-chloro-4-cyano-5-methyl-phenyl, 2,4-dichloro-5-methoxy-phenyl, 2,4-dichloro-5-ethoxy-phenyl, 2,4-dichloro-5-n-propoxy-phenyl, 2,4-dichloro-5-i-propoxy-phenyl, 4-chloro-2-fluoro-5-methoxy-phenyl, 4-chloro-2-fluoro-5-ethoxy-phenyl, 4-chloro-2-fluoro-5-n-propoxy-phenyl, 4-chloro-2-fluoro-5-i-propoxy-phenyl, 2-fluoro-4-cyano-5-methyl-phenyl, 2,4-dichloro-5-methyl-phenyl, 2-chloro-4-cyano-5-trifluoromethyl-phenyl, 4-fluoro-3-trifluoro-methyl-phenyl, 2-fluoro-4-cyano-5-trifluoromethyl-phenyl, 2-chloro-4-methyl-5-trifluoromethyl-phenyl, 2-chloro-5-fluoro-4-methoxy-phenyl, 2-fluoro-4-methoxy-5-methyl-phenyl, 2,5-difluoro-4-thiocarbamoyl-phenyl, 2-chloro-4-fluoro-5-i-propoxy-phenyl, 2-fluoro-4-cyano-5-methoxy-phenyl, 2-fluoro-4-cyano-5-i-propoxy-phenyl, 2-chloro-4-cyano-5-(2-propinyloxy)-phenyl, 2-fluoro-4-cyano-5-(1-methyl-2-propinyloxy)-phenyl, 2-chloro-4-thiocarbamoyl-5-i-propoxy-phenyl, 2-fluoro-4-cyano-5-(2-propenyloxy)-phenyl, 2-fluoro4-chloro-5-(2-propenyloxy)-phenyl, 2-chloro-4-cyano-5-methylsulphonylamino-phenyl, 2-fluoro-4-cyano-5-ethyl-sulphonylamino-phenyl, 2-fluoro-4-thiocarbamoyl-5-methylsulphonyl-phenyl, 2-chloro-4-cyano-5-ethylsulphonylamino-phenyl, 2-fluoro-4-cyano-5-cyclopropylsulphonylamino-phenyl, 2-fluoro-4-cyano-5-i-propylsulphonylamino-phenyl, 2-chloro-4-thiocarbamoyl-5-ethylsulphonylamino-phenyl, 2-chloro-4-cyano-5-cyanamino-phenyl, 2-fluoro-4-cyano-5-trifluoromethylsulphonylamino-phenyl, 2-fluoro-4-cyano-5-(2,2-difluoroethylsulphonylamino)-phenyl, 2-fluoro-4-cyano-5-phenylsulphonylamino-phenyl, 2-fluoro-4-cyano-5-t-butylsulphonylamino-phenyl, 2-chloro-4-cyano-5-methoxycarbonyl-phenyl, 2-fluoro-4-cyano-5-ethoxycarbonylphenyl, 2-fluoro-4-thiocarbamoyl-5-methoxycarbonyl-phenyl, 2-chloro-4-cyano-5-(N-cyclopropyl-ethylsulphonylamino)-phenyl, 2-fluoro-4-cyano-5-(1-methyl-2-propinylthio)-phenyl, 2-fluoro-4-cyano-5-methylamino-phenyl, 2-chloro-4-thiocarbamoyl-5-methoxycarbonylmethyl-phenyl, 2-chloro-4-cyano-5-(N-methylethylsulphonylamino)-phenyl, 2-chloro-4-cyano-5-i-propoxycarbonyl-phenyl, 2-fluoro-4-cyano-5-(bis-ethylsulphonylamino)-phenyl, 2-fluoro-4-cyano-5-(N-methylsulphonyl-ethylsulphonylamino)-phenyl, 2-fluoro-4-cyano-5-(1-methoxycarbonylethoxy)-phenyl, 2-fluoro-4-cyano-5-cyclo-propyloxy-phenyl, 2-chloro-4-cyano-5-dimethylamino-phenyl, 2-fluoro-4-cyano-5-tetrahydrofurylmethoxy-phenyl, 2-fluoro-4-cyano-5-amino-phenyl, 2-fluoro-4-cyano-5-methylaminocarbonyl-phenyl, 2-fluoro-4-cyano-5-methylsulphonyloxy-phenyl, 2-chloro-4-cyano-5-difluoromethoxy-phenyl, 2-fluoro-4-cyano-5-ethoxycarbonylmethoxy-phenyl, 2-fluoro-4-cyano-5-dimethylaminocarbonyl-phenyl, 2-fluoro-4-cyano-5-cyanomethoxy-phenyl, 2-fluoro-4-cyano-5-(2-chloro-2-propenyloxy)-phenyl, 2-fluoro-4-cyano-5-hydroxy-phenyl, 2-fluoro-4-cyano-5-nitro-phenyl, 2-fluoro-4-cyano-5-diethoxyphosphorylamino-phenyl, 2-fluoro-4-cyano-5-chlorosulphonyl-phenyl, 2-fluoro-4-cyano-5-formylamino-phenyl, 2-chloro-4-cyano-5-ethoxycarbonyloxy-phenyl, 2-fluoro-4-cyano-5-diethoxyphosphorylmethoxy-phenyl, 2-chloro-4-cyano-5-hydroxy-phenyl, 2-fluoro-4-cyano-5-(N,N-diacetylamino)-phenyl, 2-fluoro-4-cyano-5-acetylamino-phenyl, 2-chloro-4-cyano-5-thiocyanato-phenyl, 2-fluoro-4-cyano-5-diethylaminooxy-phenyl, 2-fluoro-4-cyano-5-tetrahydrofuryloxy-phenyl, 2-fluoro-4-cyano-5-ureido-phenyl, 2-fluoro-4-cyano-5-dimethoxymethyleneamino-phenyl, 2-chloro-4-cyano-5-ethoxymethyleneamino-phenyl, 2-fluoro-4-cyano-5-(2-chloroethoxycarbonyloxy)-phenyl, 2-chloro-4-cyano-5-dimethylaminomethyleneamino-phenyl, 2-chloro-4-cyano-5-(perhydropyran-4-yloxy)-phenyl, 2-fluoro-4-cyano-5-(2-methoxycarbonylethyl)-phenyl, 2-chloro-4-cyano-5-(2-carboxy-2-chloro-ethyl)-phenyl, 2-fluoro-4-cyano-5-(2-chloro-2-methoxycarbonyl-ethyl)-phenyl, 2-fluoro-4-cyano-5-(2-chloro-2-s-butoxycarbonyl)-phenyl, 2-fluoro-4-cyano-5-(2-chloro-2-carbamoyl-ethyl)-phenyl, 2-fluoro-4-cyano-5-(2-chloro-2-methoxycarbonyl-1-methyl-ethyl)-phenyl, 2-fluoro-4-cyano-5-(1,2-dibromo-2-methoxycarbonyl-ethyl)-phenyl, 2-chloro-4-cyano-5-(2-chloro-2-i-propoxy-carbonyl-ethyl)-phenyl, 2,4-dichloro-5-(2-methoxycarbonyl-ethyl)-phenyl, 2-fluoro-4-cyano-5-(2-carboxy-2-chloro-ethyl)-phenyl, 2-fluoro-4-cyano-5-(2-chloro-2-ethylaminocarbonyl-ethyl)-phenyl, 2-fluoro-4-cyano-5-(2-allylaminocarbonyl-2-chloro-ethyl)-phenyl, 2-fluoro-4-cyano-5-(2-ethoxycarbonyl-ethenyl)-phenyl, 2-fluoro-4-cyano-5-(2-chloro-2-cyclopropylaminocarbonyl-ethyl)-phenyl, 2-fluoro-4-cyano-5-(2-chloro-2-dimethylaminocarbonyl-ethyl)-phenyl, 2-chloro-4-cyano-5-(2-chloro-2-ethylsulphonylaminocarbonyl-ethyl)-phenyl, 2-fluoro-4-chloro-5-(2-carboxy-ethenyl)-phenyl, 2-fluoro-4-thiocarbamoyl-5-(2-ethylaminocarbonyl-ethenyl)-phenyl, 2-fluoro-4-cyano-5-(1-ethoxycarbonyl-ethyl)-phenyl, 2-chloro-4-cyano-5-(1-ethoxy-carbonylethyl)-phenyl, 2-chloro-4-cyano-5-carboxy-phenyl, 2-fluoro4-chloro-5-(1-ethoxycarbonyl-ethyl)-phenyl, 2-fluoro-4-chloro-5-(1-i-propoxycarbonyl-ethyl)- phenyl, 2-fluoro-4-cyano-5-i-butoxy-phenyl, 2-chloro-4-cyano-5-i-butoxy-phenyl, 2-chloro-4-cyano-5-(2-methoxy-ethoxy)-phenyl, 2-fluoro-4-chloro-5-(2-methoxy-ethoxy)-phenyl, 2-fluoro-4-chloro-5-i-butoxy-phenyl, 2-fluoro-4-hydroxy-5-i-propoxy-carbonyl-phenyl, 2-fluoro-4-cyano-5-(2-oxetanyloxy)-phenyl, 2-fluoro-4-cyano-5-(2-oxetanyloxycarbonylmethoxy)-phenyl, 2-fluoro-4-cyano-5-(2-oxetanyloxy)-phenyl,
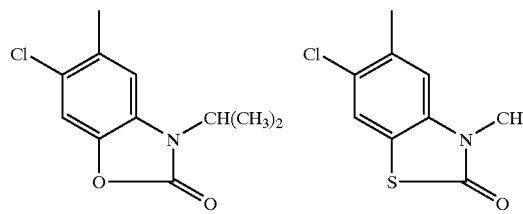
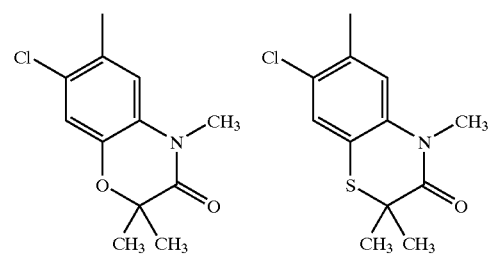
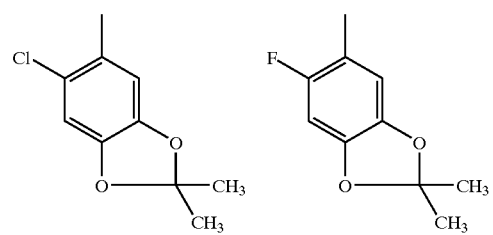
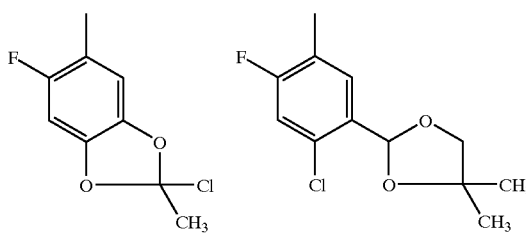
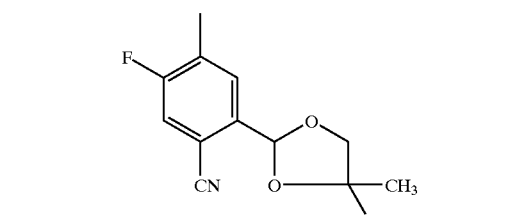
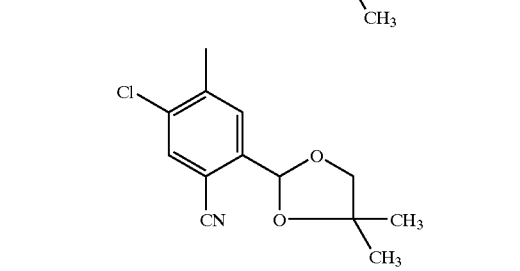
-continued
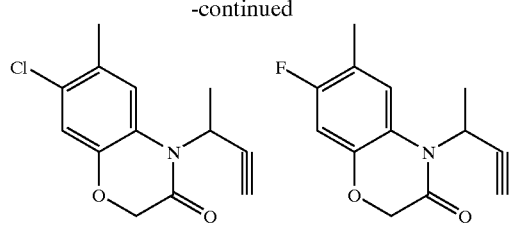
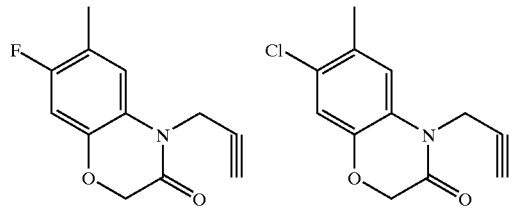
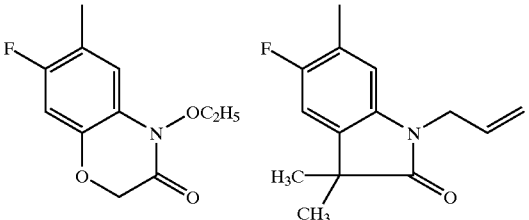
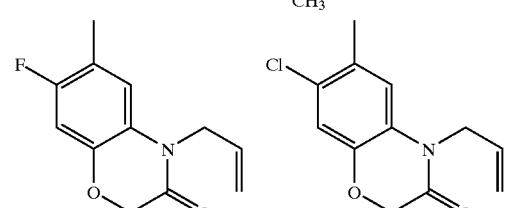
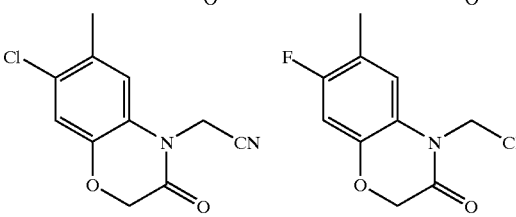
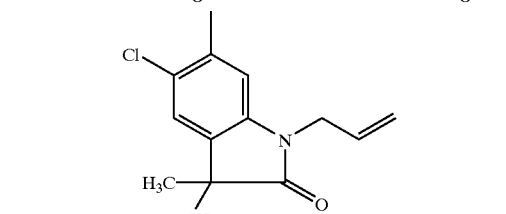
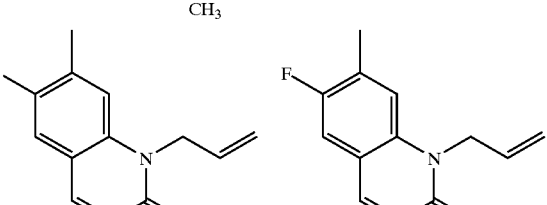
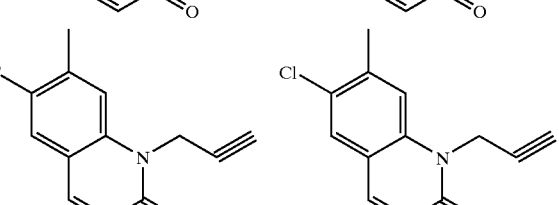
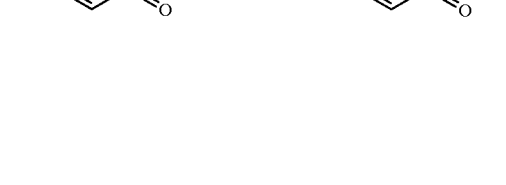

-continued

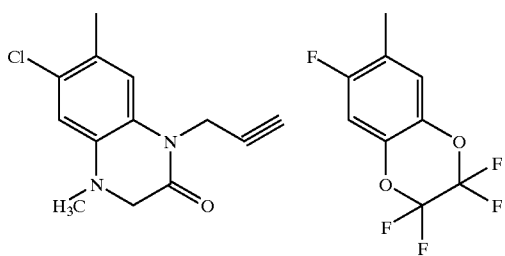

Group 2

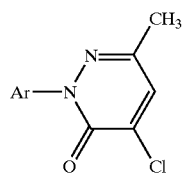
(IA-2)

Ar has for example the meanings listed above in Group 1.

Group 3

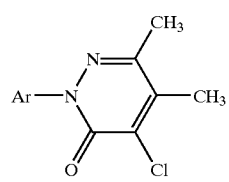
(IA-3)

Ar has for example the meanings listed above in Group 1.

Group 4

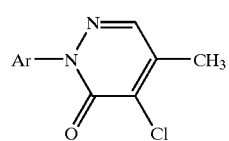
(IA-4)

Ar has for example the meanings listed above in Group 1.

Group 5

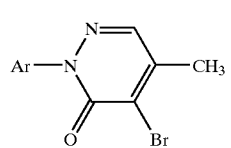
(IA-5)

Ar has for example the meanings listed above in Group 1.

Group 6

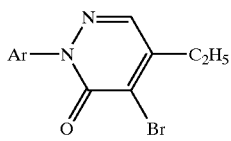
(IA-6)

Ar has for example the meanings listed above in Group 1.

Group 7

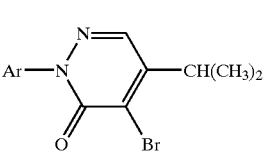
(IA-7)

Ar has for example the meanings listed above in Group 1.

Group 8

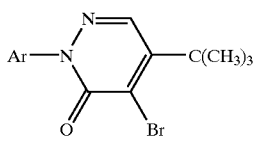
(IA-8)

Ar has for example the meanings listed above in Group 1.

Group 9

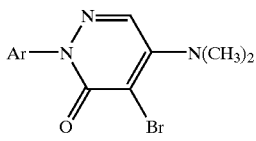
(IA-9)

Ar has for example the meanings listed above in Group 1.

Group 10

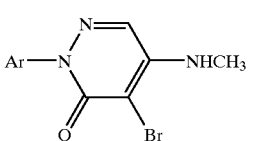
(IA-10)

Ar has for example the meanings listed above in Group 1.

Group 11

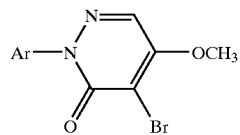
(IA-11)

Ar has for example the meanings listed above in Group 1.

Group 12

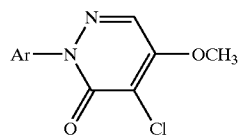
(IA-12)

Ar has for example the meanings listed above in Group 1.

Group 13

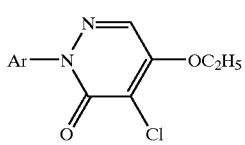
(IA-13)

Ar has for example the meanings listed above in Group 1.

Group 14 A

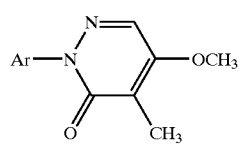
(IA-14 A)

Ar has for example the meanings listed above in Group 1.

Group 14 B

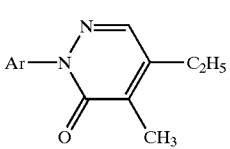
(IA-14 B)

Group 15

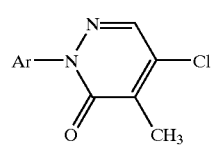
(IA-15)

Ar has for example the meanings listed above in Group 1.

Group 16

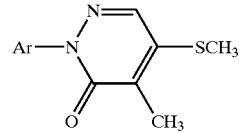
(IA-16)

Ar has for example the meanings listed above in Group 1.

Group 17

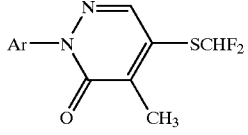
(IA-17)

Ar has for example the meanings listed above in Group 1.

Group 18

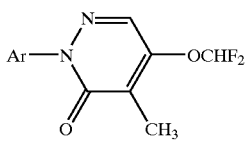
(IA-18)

Ar has for example the meanings listed above in Group 1.

Group 19

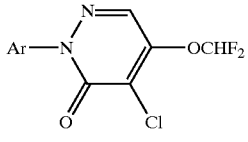
(IA-19)

Ar has for example the meanings listed above in Group 1.

Group 20

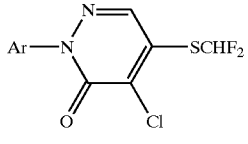
(IA-20)

Ar has for example the meanings listed above in Group 1.

Group 21

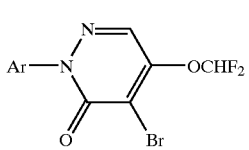
(IA-21)

Group 22

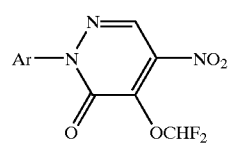
(IA-22)

Ar has for example the meanings listed above in Group 1.

Group 23

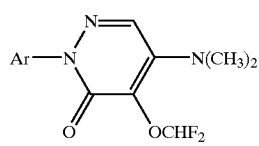
(IA-23)

Ar has for example the meanings listed above in Group 1.

Group 24

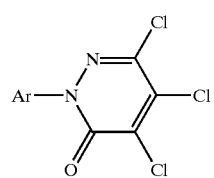
(IA-24)

Ar has for example the meanings listed above in Group 1.

Group 25

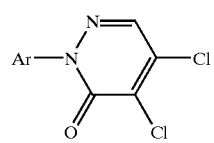
(IA-25)

Ar has for example the meanings listed above in Group 1.

Group 26

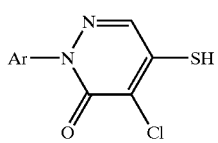
(IA-26)

Ar has for example the meanings listed above in Group 1.

Group 27

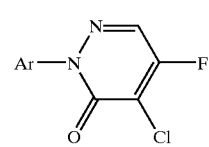
(IA-27)

Ar has for example the meanings listed above in Group 1.

Group 28

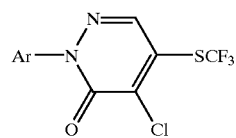
(IA-28)

Ar has for example the meanings listed above in Group 1.

Group 29

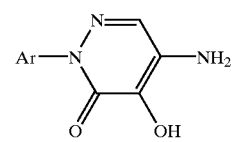
(IA-29)

Ar has for example the meanings listed above in Group 1.

Group 30

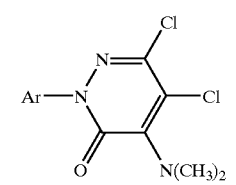
(IA-30)

Ar has for example the meanings listed above in Group 1.

Group 31

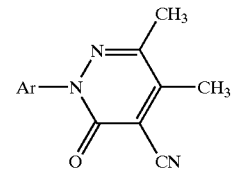
(IA-31)

Ar has for example the meanings listed above in Group 1.

Group 32

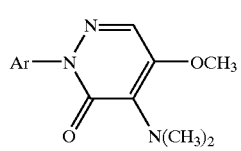
(IA-32)

Ar has for example the meanings listed above in Group 1.

Group 33

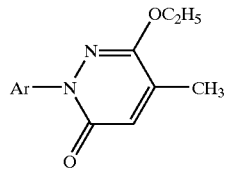
(IA-33)

Ar has for example the meanings listed above in Group 1.

Group 34

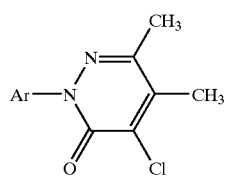
(IA-34)

Ar has for example the meanings listed above in Group 1.

Group 35

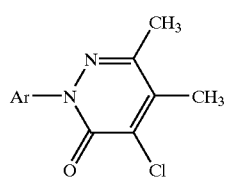
(IA-35)

Ar has for example the meanings listed above in Group 1.

Group 36

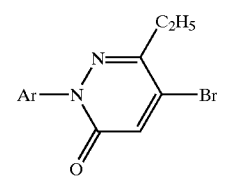
(IA-36)

Ar has for example the meanings listed above in Group 1.

Group 37

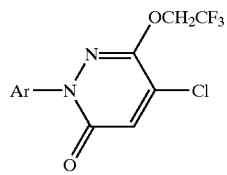
(IA-37)

Ar has for example the meanings listed above in Group 1.

Group 38

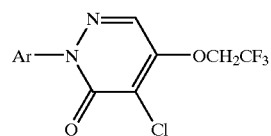
(IA-38)

Ar has for example the meanings listed above in Group 1.

Group 39

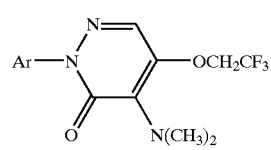
(IA-39)

Ar has for example the meanings listed above in Group 1.

Group 40

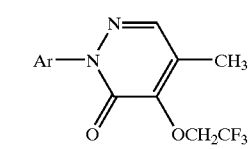
(IA-40)

Ar has for example the meanings listed above in Group 1.

Group 41

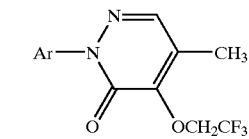
(IA-41)

Ar has for example the meanings listed above in Group 1.

Using, for example, 4-fluoro-6-methyl-pyridazin-3-one and 4,5-difluoro-2-methoxy-benzonitrile as starting materials, the course of the reaction in the process (a) according to the invention can be illustrated by the following scheme:

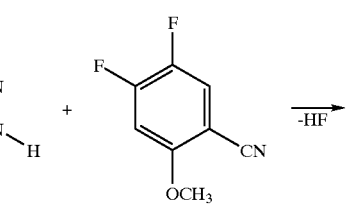

-continued

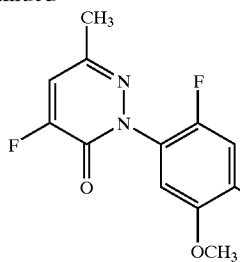

Using, for example, 4,4,4-trichloro-3-methyl-crotonal dehyde and 2,4-dichloro-5-trifluoromethyl-phenylhydrazine as starting materials, the course of the reaction in the process (b) according to the invention can be illustrated by the following scheme:

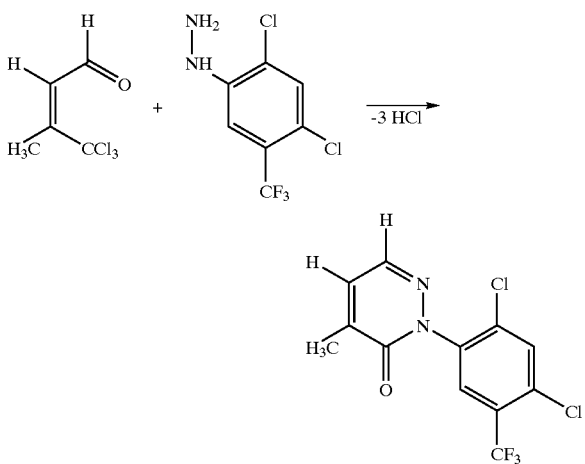

Using, for example, N-(4-bromo-2-fluoro-5-methoxy-carbonyl-phenyl)-hydrazone mucochloric acid as starting material, the course of the reaction in the process (c) according to the invention can be illustrated by the following scheme:

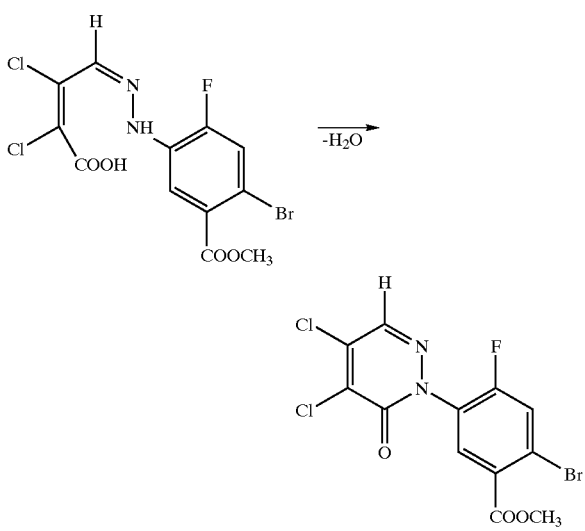

Using, for example, 2-(2,4-dichloro-phenyl)-4,5,6-trichloro-pyridazin-3-one and nitric acid as starting materials, the course of the reaction in the process (d) according to the invention can be illustrated by the following scheme:

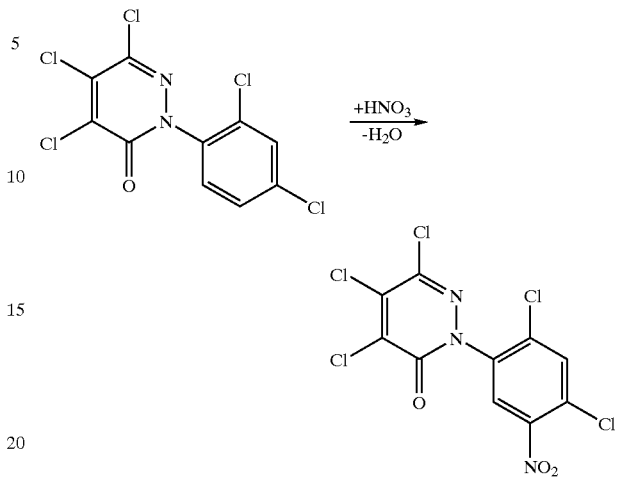

The formula (II) provides a general definition of the halogenoarenes to be used as starting materials in the process (a) according to the invention for preparing the compounds of the formula (I). In the formula (II), $R^1$, $R^2$ and $R^3$ each preferably or in particular have those meanings which have already been indicated above, in connection with the description of the compounds of the formula (I) to be prepared according to the invention, as being preferred or particularly preferred for $R^1$, $R^2$ and $R^3$; $X^1$ preferably represents fluorine, chlorine or bromine, in particular fluorine.

The starting materials of the formula (II) are known and/or can be prepared by known processes (cf. EP 191181, EP 370332, EP 431373, EP 441004).

The formula (III) provides a general definition of the pyridazinones further to be used as starting materials in the process (a) according to the invention. In the formula (III), $R^4$, $R^5$ and $R^6$ each preferably or in particular have those meanings which have already been indicated above, in connection with the description of the compounds of the formula (I) to be prepared according to the invention, as being preferred or particularly preferred for $R^4$, $R^5$ and $R^6$.

The starting materials of the formula (III) are known and/or can be prepared by known processes (cf. J. Chem. Soc. 1947, 239; Angew. Chem. 77 (1965), 282, Monatsh. Chem. 120 (1989), 329).

The formula (IV) provides a general definition of the arylhydrazines to be used as starting materials in the process (b) according to the invention for preparing the compounds of the formula (I). In the formula (IV), $R^1$, $R^2$ and $R^3$ each preferably or in particular have those meanings which have already been indicated above, in connection with the description of the compounds of the formula (I) to be prepared according to the invention, as being preferred or particularly preferred for $R^1$, $R^2$ and $R^3$.

The starting materials of the formula (IV) are known and/or can be prepared by known processes (cf. EP 370332).

The formula (V) provides a general definition of the β-trihalomethyl-enones further to be used as starting materials in the process (b) according to the invention. In the formula (V), $R^4$, $R^5$ and $R^6$ each preferably or in particular have those meanings which have already been indicated above, in connection with the description of the compounds of the formula (I) to be prepared according to the invention, as being preferred or particularly preferred for $R^4$, $R^5$ and $R^6$; $X^2$ preferably represents fluorine, chlorine or bromine, in particular chlorine.

The starting materials of the formula (V) are known and/or can be prepared by known processes (cf. DE 2706700).

The formula (VI) provides a general definition of the hydrazonecarboxylic acids to be used as starting materials in the process (c) according to the invention for preparing the compounds of formula (I). In the formula (VI), $R^1$, $R^2$, $R^3$, $R^4$, $R^5$ and $R^6$ each preferably or in particular have those meanings which have already been indicated above, in connection with the description of the compounds of the formula (I) to be prepared according to the invention, as being preferred or particularly preferred for $R^1$, $R^2$, $R^3$, $R^4$, $R^5$ and $R^6$.

The starting materials of the formula (VI) have not been disclosed in the literature; as novel compounds, they form part of the subject matter of the present application.

The novel hydrazonecarboxylic acids of the general formula (VI) are obtained when arylhydrazines of the general formula (IV)

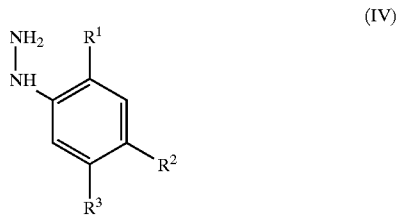

(IV)

in which $R^1$, $R^2$ and $R^3$ are each as defined above are reacted with β-carboxy-enones of the general formula (VII)

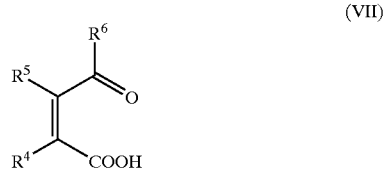

(VII)

in which $R^4$, $R^5$ and $R^6$ are each as defined above, if appropriate in the presence of a diluent such as, for example, ethanol, and if appropriate in the presence of a reaction auxiliary such as, for example, p-toluene-sulphonic acid, at temperatures between 0° C. and 100° C. (cf. the Preparation Examples).

The formula (Ia) provides a general definition of the 2,4-disubstituted phenyl-pyridazinones to be used as starting materials in the process (d) according to the invention for preparing the compounds of the formula (I). In the formula (Ia), $R^1$, $R^2$, $R^4$, $R^5$ and $R^6$ each preferably or in particular have those meanings which have already been indicated above, in connection with the description of the compounds of the formula (I) to be prepared according to the invention, as being preferred or particularly preferred for $R^1$, $R^2$, $R^4$, $R^5$ and $R^6$.

The starting materials of the formula (Ia) are known and/or can be prepared by known processes (cf. the processes (a) to (c) according to the invention).

The processes (a), (b), (c) and (d) for preparing the compounds of the formula (I) according to the invention are preferably carried out in the presence of a diluent. Suitable diluents are generally the customary organic solvents. These preferably include aliphatic, alicyclic and aromatic, optionally halogenated hydrocarbons such as, for example, pentane, hexane, heptane, petroleum ether, ligroin, benzine, benzene, toluene, xylene, chlorobenzene, dichlorobenzene, cyclohexane, methylcyclohexane, dichloromethane (methylene chloride), trichloromethane (chloroform) or carbon tetrachloride, dialkyl ethers such as, for example, diethyl ether, diisopropyl ether, methyl t-butyl ether, ethyl t-butyl ether, methyl t-pentyl ether (MTBE), ethyl t-pentyl ether, tetrahydrofuran (THF), 1,4-dioxane, ethylene glycol dimethyl ether or ethylene glycol diethyl ether, diethylene glycol dimethyl ether or diethylene glycol diethyl ether; dialkyl ketones such as, for example, acetone, butanone (methyl ethyl ketone), methyl i-propyl ketone or methyl i-butyl ketone, nitriles such as, for example, acetonitrile, propionitrile, butyronitrile or benzonitrile; amides such as, for example, N,N-dimethyl-formamide (DMF), N,N-dimethyl-acetamide, N-methyl-formanilide, N-methyl-pyrrolidone or hexamethyl-phosphoric triamide; esters such as, for example, methyl acetate, ethyl acetate, n- or i-propyl acetate, n-, i- or s-butyl acetate; sulphoxides such as, for example, dimethyl sulphoxide; alkanols such as, for example, methanol, ethanol, n- or i-propanol, n-, i-, s- or t-butanol, ethylene glycol monomethyl ether or ethylene glycol monoethyl ether, diethylene glycol monomethyl ether or diethylene glycol monoethyl ether; their mixtures with water or pure water. In the process (b) according to the invention, acetic acid may also be used advantageously as diluent.

The processes (a) and (b) according to the invention for preparing the compounds of the formula (I) are preferably carried out in the presence of a suitable reaction auxiliary. Suitable reaction auxiliaries are generally the customary inorganic or organic bases or acid acceptors. These preferably include alkali metal or alkaline earth metal acetates, amides, carbonates, bicarbonates, hydrides, hydroxides or alkoxides such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n-, i-, s- or t-butoxide or potassium n-, i-, s- or t-butoxide, furthermore also basic organic nitrogen compounds such as, for example, trimethylamine, triethylamine, tripropylamine, tributylamine, ethyl-diisopropylamine, N,N-dimethyl-cyclohexylamine, dicyclohexylamine, ethyl-dicyclo-hexylamine, N,N—dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo[4.3.0]-non-5-ene (DBN), and 1,8-diazabicyclo[5.4.0]-undec-7-ene (DBU).

The process (c) according to the invention for preparing the compounds of the formula (I) is carried out in the presence of a dehydrating agent. Suitable for this purpose are the customary dehydrating agents such as, for example, sulphur acid, methane sulphonic acid, benzene sulphonic acid, p-toluenesulphonic acid acetic anhydride and phosphorus(V) oxide.

The process (d) according to the invention for preparing the compounds of the formula (I) is carried out using a nitrating agent. Suitable for this purpose are the customary nitrating agents such as, for example, nitric acid and mixtures thereof with nitration auxiliaries such as, for example, sulphuric acid.

When carrying out the processes (a), (b), (c) and (d) according to the invention, the reaction temperatures can be varied over a relatively wide range. In general, temperatures of between −20° C. and +200° C., preferably temperatures of between 0° C. and 150° C., in particular between 10° C. and 120° C., are employed.

The process according to the invention is generally carried out under atmospheric pressure. However, it is also possible to operate under elevated or reduced pressure—in general between 0.1 bar and 10 bar.

In the practice of the processes (a), (b), (c) and (d) according to the invention, the starting materials are generally employed in approximately equimolar amounts. However, it is also possible to use one of the components in a relatively large excess. The reaction is generally carried out in a suitable diluent, if appropriate in the presence of a reaction auxiliary, and the reaction mixture is generally stirred for several hours at the temperature required. Work-up is carried out according to customary methods (cf. the Preparation Examples).

The active compounds according to the invention can be used as defoliants, desiccants, haulm-killers and, especially, as weed-killers. Weeds, in the broadest sense, are to be understood as meaning all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita. Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual crops.

The compounds of the formula (I) according to the invention are particularly suitable for the selective control of dicotyledonous weeds in monocotyledonous and dicotyledonous crops, both by the pre- and the post-emergence method.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formiers.

If the extender used is water, it is also possible to use for example organic solvents as auxiliary solvents. Essentially, suitable liquid solvents include: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkyl-aryl polyglycol ethers, alkylsulphonates, alkyl sulphates, arylsulphonates and protein hydrolysates; suitable dispersants are: for example lignin-sulphite waste liquors and methyl cellulose.

Tackifiers such as carboxymethyl cellulose and natural and synthetic polymers in the form of powders, granules or latices, such as gum arabic, polyvinyl alcohol and polyvinyl acetate, and natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be used as such or, in their formulations, as a mixture with known herbicides for the control of weeds, in which case ready-to-use formulations or tank mixes are possible.

Suitable co-components for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacet-anilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxy-lamines such as, for example, alloxydim, clethodim, cycloxydim, sethoxydim and tralkoxydim; imidazolinones such as, for example, imazethapyr, imazamethabenz, imaza-pyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, diallate, EPTC, esprocarb, molinate, prosulfocarb, thioben-carb and triallate; triazines such as, for example, atrazine, cyanazine, simazine, simetryne, terbutryne and terbutyla-zine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the application rates are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

(Process (a))

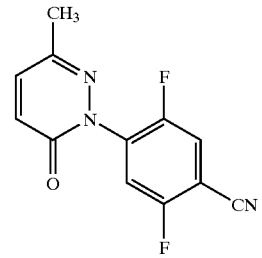

20 g (0.10 mol) of 3-methyl-pyridazine-6-one hydrobromide and 30 g (0.22 mol) of potassium carbonate are initially charged in 200 ml of dimethyl sulphoxide, and 15.7 g (0.10 mol) of 2,4,5-trifluorobenzonitrile are added at room temperature (about 20° C.). The mixture is stirred at 40° C.–50° C. overnight and subsequently concentrated using a rotary evaporator. The residue is stirred with water, filtered off with suction and recrystallized from isopropanol.

18.5 g (76% of theory) of 2-(2,5-difluoro-4-cyano-phenyl)-6-methyl-pyridazin-3-one of melting point 159° C. are obtained.

Example 2

(Process (a))

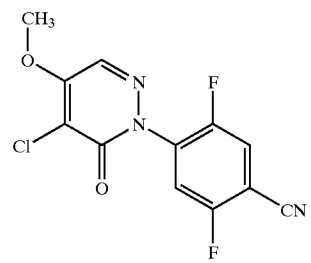

5.0 g (0.03 mol) of 5-chloro-4-methoxy-pyridazine-6-one and 5.0 g of potassium carbonate are initially charged in 50 ml of dimethyl sulphoxide, and 4.7 g (0.03 mol) of 2,4,5-trifluoro-benzonitrile are added at room temperature (about 20° C.). The mixture is stirred at room temperature for 2 hours and then poured into water, and precipitated product is filtered off with suction, washed with water and dried.

7.7 g (86% of theory) of 2-(2,5-difluoro-4-cyano-phenyl)-4-chloro-5-methoxy-pyridazin-3-one of melting point 182° C. are obtained.

Example 3

(Process (b))

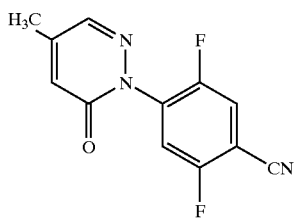

At room temperature (about 20° C.), 7.9 g (0.047 mol) of 2,5-difluoro-4-cyano-phenylhydrazine are added to 8.8 g (0.047 mol) of 4,4,4-trichloro-2-methyl-crotonaldehyde, 11.5 g (0.14 mol) of sodium acetate and 20 ml of water in 100 ml of acetic acid, and the mixture is stirred at 50° C. overnight. The mixture is allowed to cool to room temperature, stirred with water and filtered off with suction, and the residue is recrystallized from n-hexane.

7.2 g (62% of theory) of 2-(2,5-difluoro-4-cyano-phenyl)-5-methyl-pyridazin-3-one of melting point 223° C. are obtained.

Example 4

(Process (c))

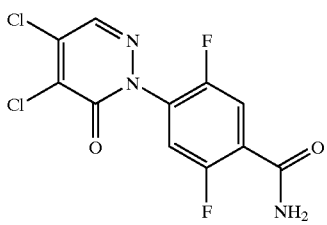

25.9 g (0.081 mol) of 2,5-difluoro-4-cyano-phenylhydrazone mucochloric acid in 100 ml of 96% strength sulphuric acid are slowly heated to 80° C. and then stirred for 1 hour and subsequently stirred with 1 litre of ice-water, and precipitated product is filtered off with suction and washed with water. The residue is stirred with 200 ml of hot ethanol, filtered cold with suction, washed and dried.

21 g (81% of theory) of 2-(2,5-difluoro-4-aminocarbonyl-phenyl)-4,5-dichloro-pyridazine-3-one of melting point>260° C. are obtained.

Example 5

(Process (d))

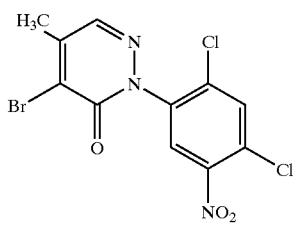

At 0° C.–5° C., 2 ml of 98% strength nitric acid are added dropwise to 5.9 g (0.018 mol) of 2-(2,4-dichloro-phenyl)-4-bromo-5-methyl-pyridazin-3-one in 20 ml of 96% strength sulphuric acid. The mixture is stirred at room temperature (about 20° C.) for 8 hours and the product is precipitated with ice-water, filtered off with suction, washed neutral with water and dried.

5.6 g (82% of theory) of 2-(2,4-dichloro-5-nitro-phenyl)-4-bromo-5-methyl-pyridazin-3-one of melting point 155° C. (decomposition) are obtained.

Example 6

(Process (d))

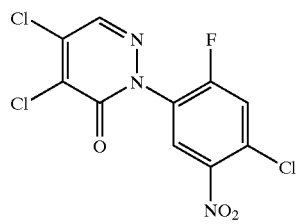

At 0° C.–10° C., 29.35 g (0.10 mol) of 2-(2-fluoro-4-chloro-phenyl)-4,5-dichloro-pyridazin-3-one are introduced into 60 ml of 96% strength sulphuric acid. At the same temperature, 12 ml of 98% strength nitric acid are added dropwise over a period of 20 minutes, and the mixture is then stirred at room temperature (about 20° C.) for 3 hours. The mixture is poured into 600 ml of ice-water and precipitated product is filtered off with suction, washed neutral with water and subsequently washed with ethanol.

31.5 g (94% of theory) of 2-(2-fluoro-4-chloro-5-nitro-phenyl)-4,5-dichloro-pyridazin-3-one of melting point 168° C. are obtained.

Example 7

At room temperature (about 20° C.), 1.68 g (0.03 mol) of propargyl alcohol in 50 ml of acetonitrile are stirred for 15 minutes with 0.9 g (0.03 mol) of sodium hydride (80%), subsequently, 3.7 g (0.015 mol) of 2-(2,5-difluoro-4-cyano-phenyl)-6-methyl-pyridazin-3-one are added to the mixture, which is stirred at room temperature for a further 5 hours, poured into water and acidified with concentrated hydrochloric acid. Precipitated product is filtered off with suction and recrystallized from methanol.

1.26 g (27% of theory) of 2-(2-fluoro-4-cyano-5-propargyloxy-phenyl)-6-methyl-pyridazin-3-one of melting point 180° C. are obtained.

Example 8

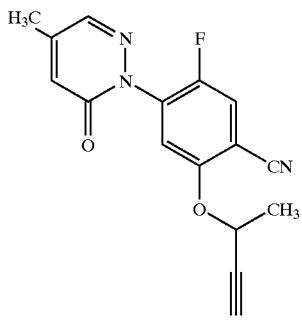

At room temperature (about 20° C.), 1.1 g (0.015 mol) of butin-1-ole-(3) in 50 ml of acetonitrile are stirred for 15 minutes with 0.45 g (0.015 mol) of sodium hydride (80%), subsequently, 2.5 g (0.01 mol) of 2-(2,5-difluoro-4-cyano-phenyl)-5-methyl-pyridazin-3-one are added to the mixture, which is then stirred at room temperature overnight, poured into water and acidified with concentrated hydrochloric acid. Precipitated product is filtered off with suction and dried.

2.6 g (88% of theory) of 2-(2-fluoro-4-cyano-5-but-1-ine-3-yl-oxy-phenyl)-5-methyl-pyridazin-3-one of melting point 108° C. are obtained.

Example 9

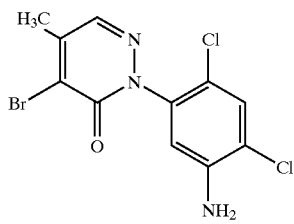

At room temperature (about 20° C.), 7.3 g (0.13 mol) of iron powder are added a little at a time to a mixture of 4.8 g (0.013 mol) of 2-(2,4-dichloro-5-nitro-phenyl)-4-bromo-5-methyl-pyridazin-3-one in 100 ml of acetic acid, 50 ml of water and 15 ml of ethyl acetate. The reaction mixture is stirred at room temperature for 12 hours and the solid is filtered off with suction. The residue is washed with water and ethyl acetate. The filtrate is subsequently shaken with sodium bicarbonate solution and the organic phase is dried over sodium sulphate and concentrated.

0.9 g (20% of theory) of 2-(2,4-dichloro-5-amino-phenyl)-4-bromo-5-methyl-pyridazin-3-one of melting point 211° C. is obtained.

Example 10

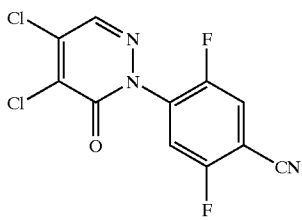

At 70° C., 39 g (0.30 mol) of thionyl chloride are added dropwise over a period of 1 hour to 53 g (0.166 mol) of 2-(2,5-difluoro-4-carboxamido-phenyl)-4,5-dichloro-pyridazin-3-one in 300 ml of toluene and 2 ml of dimethylformamide. The mixture is stirred at reflux temperature for about 90 minutes, filtered hot and allowed to cool. Precipitated product is filtered off with suction, washed with toluene and dried.

35 g (70% of theory) of 2-(2,5-difluoro-4-cyano-phenyl)-4,5-dichloro-pyridazin-3-one of melting point 206° C. are obtained.

Example 11

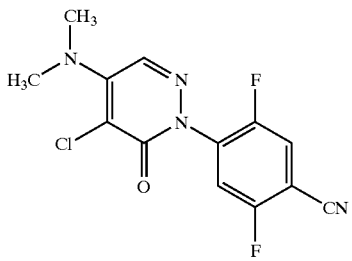

A mixture of 4.22 g (0.014 mol) of 2-(2,5-difluoro-4-cyano-phenyl)-4,5-dichloro-pyridazin-3-one, 1.38 g (0.017 mol) of dimethylamine hydrochloride and 3.1 g (0.03 mol) of triethylamine in 50 ml of acetonitrile is stirred at room temperature (about 20° C.) overnight (about 15 hours), then poured into water, filtered off with suction and washed with water and then with isopropanol.

3.35 g (77% of theory) of 2-(2,5-difluoro-4-cyano-phenyl)-4-chloro-5-dimethyl-amino-pyridazin-3-one of melting point 158° C. are obtained.

Example 12

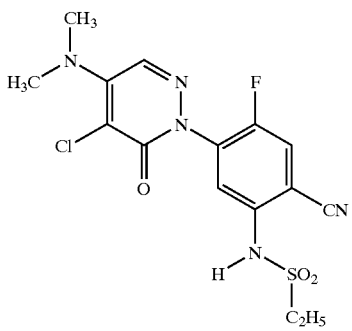

At 110° C., 1.55 g (5 mmol) of 2-(2,5-difluoro-4-cyano-phenyl)-4-chloro-5-dimethylamino-pyridazin-3-one, 0.9 g (6 mmol) of potassium carbonate and 0.65 g (6 mmol) of ethanesulphonamide in 10 ml of dimethyl sulphoxide are stirred for 8 hours. The mixture is concentrated, stirred with water and acidified with concentrated hydrochloric acid, precipitated product is filtered off with suction and the residue is purified by column chromatography (eluent: cyclohexane/ethyl acetate 1:1).

0.6 g (30% of theory) of 2-(4-cyano-2-fluoro-5-ethylsulphonylamino-phenyl)-4-chloro-5-dimethylamino-pyridazin-3-one of melting point 206° C. is obtained.

Example 13

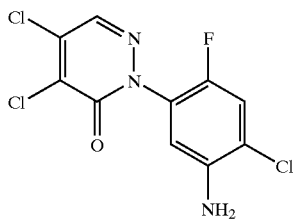

50.4 g (0.9 mol) of iron powder are added a little at a time to 29.5 g (0.0875 mol) of 2-(2-fluoro-4-chloro-5-nitro-phenyl)-4,5-dichloro-pyridazin-3-one, 200 ml of acetic acid, 100 ml of water and 30 ml of ethyl acetate. By occasional cooling, the temperature is kept at a maximum of 50° C. The mixture is stirred at room temperature (about 20° C.) for 2 hours, filtered with suction and washed with ethyl acetate. By adding water, a solid product is precipitated from the filtrate. The solid is filtered off with suction, washed with water and then with ethanol.

15 g (56% of theory) of 2-(2-fluoro-4-chloro-5-amino-phenyl)-4,5-dichloro-pyridazin-3-one of melting point 186° C. are obtained.

Example 14

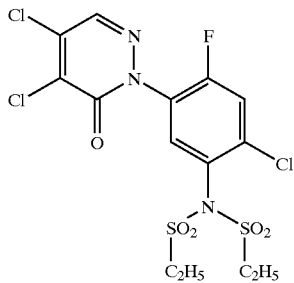

12 g (0.04 mol) of 2-(2-fluoro4-chloro-5-amino-phenyl)-4,5-dichloro-pyridazin-3-one and 24 g (0.24 mol) of triethylamine in 300 ml of methylene chloride are cooled to −10° C. and 31 g (0.24 mol) of ethanesulphonyl chloride are added dropwise over a period of 15 minutes. The mixture is stirred at −10° C. for 30 minutes and then at room temperature for 3 hours and admixed with water. The organic phase is separated off, dried over sodium sulphate and concentrated, and the residue is recrystallized from isopropanol.

14.9 g (76% of theory) of 2-[2-fluoro-4-chloro-5-(bis-ethylsulphonyl)-amino-phenyl]-4,5-dichloro-pyridazin-3-one of melting point 188° C. are obtained.

By the methods of Examples 1 to 14 and according to the general description of the preparation process according to the invention, it is also possible to prepare, for example, the compounds of the formula (I) listed in Table 1 below.

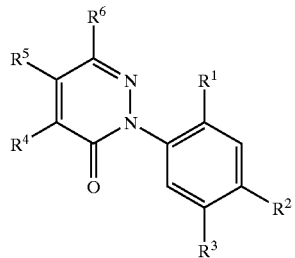

(I)

TABLE 1

Examples of compounds of the formula (I)

| Ex. No. | $R^1$ | $R^2$ | $R^3$ | $R^4$ | $R^5$ | $R^6$ | Melting point (° C.) |
|---|---|---|---|---|---|---|---|
| 15 | F | CN | $NHSO_2C_2H_5$ | H | H | $CH_3$ | 182 |
| 16 | F | CN | $OCH(CH_3)C≡CH$ | H | H | $CH_3$ | 132 |
| 17 | Cl | Cl | $NO_2$ | Cl | Cl | H | 170 |
| 18 | Cl | Cl | $NH_2$ | Cl | Cl | H | 235 |
| 19 | Cl | Cl | $N(SO_2C_2H_5)_2$ | Cl | Cl | H | 226 |
| 20 | Cl | Cl | $NHSO_2C_2H_5$ | Cl | $OCH_3$ | H | 204 |
| 21 | F | CN | F | OH | $NO_2$ | H | 180 |
| 22 | F | CN | F | Cl | $NHCH_3$ | H | 263 |
| 23 | F | Cl | $NHSO_2C_2H_5$ | Cl | Cl | H | 175 |
| 24 | F | CN | F | Cl | OH | H | 260 |
| 25 | F | CN | $NHSO_2C_2H_5$ | Cl | $NHCH_3$ | H | 195 |
| 26 | F | CN | $OCH(CH_3)C≡CH$ | Cl | $NHCH_3$ | H | 98 |
| 27 | F | Cl | $NHSO_2CH_3$ | Cl | Cl | H | 200 |
| 28 | F | CN | $OC_2H_5$ | H | H | $CH_3$ | 179 |
| 29 | F | CN | $OCH(C_2H_5)C≡CH$ | H | H | $CH_3$ | 126 |
| 30 | Cl | Cl | $NO_2$ | H | $CH_3$ | H | 148 |
| 31 | F | CN | $NHSO_2C_2H_5$ | H | $CH_3$ | H | 131 |
| 32 | Cl | Cl | $NH_2$ | H | $CH_3$ | H | 178 |
| 33 | Cl | Cl | $N(SO_2C_2H_5)_2$ | H | $CH_3$ | H | 238 |
| 34 | Cl | Cl | $NHSO_2C_2H_5$ | H | $CH_3$ | H | 201 |
| 35 | F | CN | $OCH(C_2H_5)C≡CH$ | H | $CH_3$ | H | 86 |
| 36 | F | CN | $OC_3H_7$-i | H | $CH_3$ | H | 85 |
| 37 | F | CN | $OCH_2C≡CH$ | H | $CH_3$ | H | 177 |
| 38 | F | CN | $NHSO_2CH_3$ | H | $CH_3$ | H | 82 |

TABLE 1-continued

Examples of compounds of the formula (I)

| Ex. No. | R¹ | R² | R³ | R⁴ | R⁵ | R⁶ | Melting point (° C.) |
|---|---|---|---|---|---|---|---|
| 39 | F | Cl | N(SO₂C₂H₅)₂ | SCH₃ | SCH₃ | H | 220 |
| 40 | F | Cl | N(SO₂C₂H₅)₂ | Cl | N(CH₃)₂ | H | 156 |
| 41 | F | CN | OCH₂C≡CH | Cl | N(CH₃)₂ | H | 199 |
| 42 | F | CN | F | Br | Br | H | 202 |
| 43 | F | CN | OCH₂C≡CH | Cl | NHCH₃ | H | 222 |
| 44 | F | CN | OCH(CH₃)C≡CH | Cl | N(CH₃)₂ | H | 151 |
| 45 | F | CSNH₂ | NHSO₂C₂H₅ | H | H | CH₃ | 205 |

Starting Materials of the Formula (Ia)

Example (Ia-1)

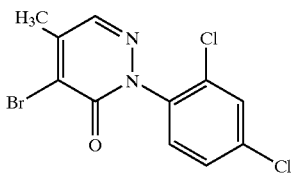

At room temperature (about 20° C.), 10.1 g (47 mmol) of 2,4-dichloro-phenyl-hydrazine hydrochloride are added to 12.5 g (47 mmol) of 4,4,4-trichloro-3-bromo-2-methyl-crotonaldehyde, 11.5 g (140 mmol) of sodium acetate and 40 ml of water in 150 ml of acetic acid, and the mixture is stirred at 40° C. overnight. The mixture is allowed to cool to room temperature, stirred with water and filtered with suction.

7.5 g (48% of theory) of 2-(2,4-dichloro-phenyl)-4-bromo-5-methyl-pyridazin-3-one of melting point 108° C. are obtained.

Example (Ia-2)

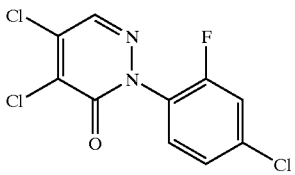

56.2 g (0.35 mol) of 2-fluoro-4-chloro-phenyl-hydrazine, 67.6 g of mucochloric acid and 2 g of p-toluenesulphonic acid in 700 ml of ethanol are stirred at reflux temperature for 12 hours and then allowed to cool. Precipitated product is filtered off with suction, washed with ethanol and dried.

69.8 g (68% of theory) of 2-(2-fluoro-4-chloro-phenyl)-4,5-dichloro-pyridazin-3-one of melting point 158° C. are obtained.

Starting Materials of the Formula (VI):

Example (VI-1)

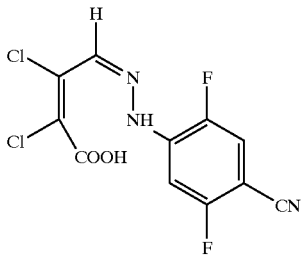

84.5 g (0.5 mol) of 2,5-difluoro-4-cyano-phenyl-hydrazine are initially charged in 700 ml of ethanol and 84.5 g (0.6 mol) of mucochloric acid are introduced with stirring. The exothermic reaction, which sets in slowly, reaches 50° C. after 30 minutes. After the reaction has subsided, 1 g of p-toluenesulphonic acid is added, the mixture is stirred at reflux temperature for 12 hours, and the precipitated solid is filtered cold with suction and washed with ethanol.

133 g (83% of theory) of 2,5-difluoro-4-cyano-phenyl-hydrazone mucochloric acid of melting point >260° C. are obtained.

Use Examples

In the use examples, the compounds (A) and (B) listed below are used as comparative substances.

(A)

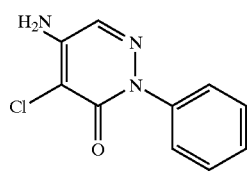

5-Amino-4-chloro-2-phenyl-pyridazin-3-one (known from DE 1105232);

(B)

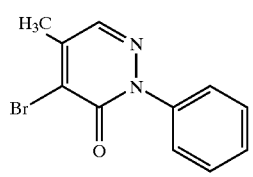

4-Bromo-5-methyl-2-phenyl-pyridazin-3-one (known from DE 2706700).

Example A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is watered or sprayed with the preparation of the active compound. It is advantageous to keep the amount of water per unit area constant. The concentration of the active compound in the preparation is immaterial, only the amount of active compound applied per unit area matters.

After three weeks, the degree of damage to the plants is rated in % damage by comparison with the development of the untreated control.

The figures denote:

0%=no effect (like untreated control)

100%=total destruction

In this test, strong activity against weeds such as, for example, Abutilon (100%), Chenopodium (90–100%), Galinsoga (80–100%) and Solanum (60–100%) is shown, for example, by the compounds of Preparation Examples 3, 7, 8, 15, 16, 25, 29, 31, 34, 35, 36 and 41 at an application rate between 125 and 500 g/ha, combined with good crop safety in crops such as sunflowers (0–20%) and maize (0–10%).

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area.

After three weeks, the degree of damage to the plants is rated in % damage by comparison with the development of the untreated control.

The figures denote:

0%=no effect (like untreated control)

100%=total destruction

TABLE A

Pre-emergence test/greenhouse

| Compound of Preparation Example No. | Application rate (g ai./ha) | Maize | Sun-flower | Abu-tilon | Cheno-podium | Galin-soga | Sola-num |
|---|---|---|---|---|---|---|---|
| (B) | 500 | 0 | 0 | 0 | 50 | 30 | 50 |
| (A) | 500 | 0 | 100 | 20 | 50 | — | 40 |
| (15) | 500 | 0 | 0 | 100 | 100 | 80 | 95 |
| (16) | 500 | 10 | 20 | 100 | 100 | 100 | 100 |
| (25) | 500 | 0 | — | 100 | 90 | 100 | 60 |
| (7) | 250 | 0 | 20 | 100 | 100 | 95 | 100 |
| (29) | 500 | 0 | 0 | 100 | 100 | 100 | 100 |
| (3) | 250 | 0 | 0 | 100 | — | 100 | 90 |
| (8) | 250 | 0 | 0 | 100 | 100 | 100 | 100 |
| (31) | 250 | 0 | 0 | 100 | — | 80 | 100 |
| (34) | 500 | 0 | 20 | 100 | 100 | 100 | 90 |
| (35) | 250 | 0 | — | 100 | 100 | 100 | 100 |
| (36) | 250 | 10 | — | 100 | 100 | 90 | 100 |
| (41) | 125 | 10 | 0 | 100 | 100 | 100 | 100 |

Example B

Post-emergence test

Solvent: 5 parts by weight of acetone

Emulsifier: 1 part by weight of alkylaryl polyglycol ether

In this test, strong activity against weeds such as Amaranthus (60–100%), Polygonum (80–100%) and Veronica (90–100%) is shown, for example, by the compounds of Preparation Examples 8, 15, 16, 31, 35, 37 and 41 at an application rate between 60 and 250 g/ha, combined with largely good crop safety in crops such as wheat (0–20%).

TABLE B

Post-emergence test/greenhouse

| Compound of Preparation Example No. | Application rate (g ai./ha) | Wheat | Amaran-thus | Cheno-podium | Datura | Poly-gonum | Vero-nica |
|---|---|---|---|---|---|---|---|
| (B) | 250 | 30 | 30 | 50 | 80 | 50 | 40 |
| (15) | 250 | 5 | 100 | 95 | 90 | 80 | 95 |
| (16) | 60 | 5 | 100 | 95 | 100 | 95 | 90 |
| (8) | 60 | 0 | 90 | 95 | 100 | 100 | 100 |
| (31) | 60 | 5 | 100 | 80 | 100 | 90 | 90 |
| (35) | 60 | 20 | 95 | 95 | 100 | 90 | 95 |
| (37) | 125 | 20 | 100 | 100 | 100 | 100 | 100 |
| (41) | 250 | 20 | 60 | 90 | 100 | 100 | 100 |

What is claimed is:

1. A phenylpyridazinone of the formula (I)

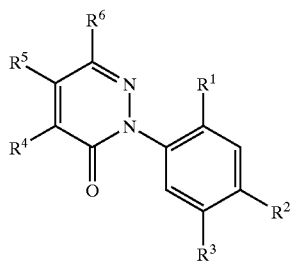

(I)

wherein

R$^1$ represents fluorine, chlorine or bromine,

R$^2$ represents cyano, carbamoyl, thiocarbamoyl, fluorine, chlorine or bromine or represents respectively optionally fluorine- or chlorine-substituted alkyl, alkoxy or alkylthio having in each case 1 or 2 carbon atoms, R$^3$ represents A$^3$ or the grouping —NH—A$^3$ A$^3$ represents fluorine, chlorine, bromine, or represents respectively optionally fluorine-, chlorine-, C$_1$–C$_4$-alkoxy-substituted alkyl, alkoxy, alkylthio, alkylsulphinyl, alkylsulphonyl, alkylamino, dialkylamino, alkoxycarbonyl or dialkoxy(thio)phosphoryl having in each case 1 to 6 carbon atoms in the alkyl groups, or represents respectively optionally fluorine- or chlorine-substituted alkenyl, alkenyloxy, alkenylamino, alkylideneamino, alkenyloxycarbonyl, alkinyl, akinyloxy, alkinylamino or alkinyloxycarbonyl having in each case 2 to 6 carbon atoms in the alkenyl, alkylidene or alkinyl groups;

wherein at least one of R$^1$, R$^2$ and R$^3$ is not fluorine, chlorine or bromine;

R$^4$, R$^5$ and R$^6$ are identical or different and each represents hydrogen, cyano, thiocarbamoyl, nitro, hydroxyl, mercapto, amino, fluorine, chlorine, bromine or represent respectively optionally fluorine- and/or chlorine-substituted alkyl, alkoxy, alkylthio, alkylamino or dialkylamino having in each case 1 to 4 carbon atoms in the alkyl groups, except for the compound 4-chloro-5-dimethylamino-2-(4-chloro-2-fluoro-5-propargyloxy-phenyl)-pyridazin-3-one.

2. A phenylpyridazinone of the formula (I) according to claim 1 wherein

R$^1$ represents fluorine or chlorine,

R$^2$ represents cyano, thiocarbamoyl, fluorine, chlorine, bromine, methyl or trifluoromethyl, R$^3$ represents A$^3$ or the grouping —NH—A$^3$ A$^3$ represents respectively optionally fluorine, chlorine, methoxy- or ethoxy-substituted methyl, ethyl, n- or i-propyl, n-, i-, s- or t-butyl, n-, i-, s- or t-pentyl, methoxy, ethoxy, n- or i-propoxy, n-, i-, s- or t-butoxy, n-, i-, s- or t -pentyloxy, methylthio, ethylthio, n- or i-propylthio, n-, i-, s- ot t-butylthio, methylsulphinyl, ethylsulphinyl, n- or i-propylsulphinyl, methylsulfonyl, ethylsulphonyl, n- or i-propylsulphonyl, methylamino, ethyl amino, n- or i-propylamino, n-, i-, s- or t-butylamino, dimethylamnino, diethylamino, methoxycarbonyl, ethoxycarbonyl, n- or i-propoxycarbonyl, dimethoxyphosphoryl, diethoxyphosphoryl, dipropoxyphosphoryl or diisopropoxyphosphoryl, or represents respectively optionally fluorine- or chlorine-substituted propenyl, butenyl, propenyloxy, butenyloxy, propenylamino, butenylamino, propylideneamino, butylideneamino, propenyloxycarbonyl, butenyloxycarbonyl, propinyl, butinyl, propinyloxy, butinyloxy, propinylamino, butinylamino, propinyloxycarbonyl or butinyloxycarbonyl, R$^4$, R$^5$ and R$^6$ are identical or different and each represents hydrogen, cyano, thiocarbamoyl, nitro, hydroxyl, mercapto, amino, fluorine, chlorine, bromine, or represents respectively optionally fluorine- and/or chlorine-substituted methyl, ethyl, n- or i-propyl, n-, i-, s- or t-butyl, methoxy, ethoxy, methylthio, ethylthio, methylamino, ethylamino or dimethylamino, except for the compound 4-chloro-5-dimethylamino-2-(4-chloro-2-fluoro-5-propargyloxy-phenyl) pyridazin-3-one.

3. The compound of claim 1 wherein,

R$^1$=fluorine;

R$^2$=cyano;

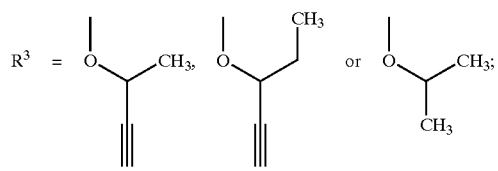

R$^4$=R$^6$=hydrogen; and

R$^5$=CH$_3$.

4. The compound of claim 1 wherein,

R$^1$=fluorine;

R$^2$=cyano;

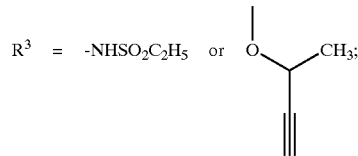

R$^4$=R$^5$=hydrogen; and

R$^6$=CH$_3$.

5. The compound of claim 1 wherein,

R$^1$=R$^2$=Cl;

R$^3$=NH(SO$_2$C$_2$H$_5$);

R$^4$=R$^6$=hydrogen; and

R$^5$=CH$_3$.

6. The compound of claim 1 wherein,

R$^1$=fluorine;

R$^2$=cyano;

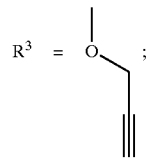

$R^4$=Cl;
$R^5$=—N(CH$_3$)$_2$; and
$R^6$=hydrogen.

7. The compound of claim 1 wherein,
$R^1$=fluorine;
$R^2$=CSNH$_2$;
$R^3$=—NH(SO$_2$C$_2$H$_5$);
$R^4$=$R^5$=hydrogen; and
$R^6$=CH$_3$.

8. The phenylpyridizanone having the formnula

9. A process for preparing a phenylpyridazinone of claim 1, comprising reacting a halogenoarene of the formula (II)

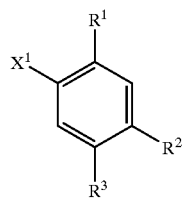

wherein $R^1$, $R^2$ and $R^3$ are each as defined in claim 1, and $X^1$ represents halogen, with a pyridazinone of the formula (III)

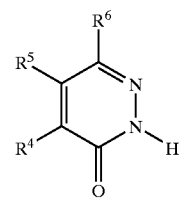

wherein $R^4$, $R^5$ and $R^6$ are each as defined in claim 2, or with an acid adduct or alkali metal salt of the pyridazinone of the formula (III).

10. An herbicidal composition comprising a herbicidally effective amount of a compound according to claim 1 and an extender or surfactant.

11. A method of controlling unwanted vegetation which comprises applying to such vegetation or to a locus from which it is desired to exclude such vegetation an herbicidally effective amount of a compound according to claim 1.

* * * * *

UNITED STATES PATENT AND TRADEMARK OFFICE
CERTIFICATE OF CORRECTION

PATENT NO. : 6,551,963 B1
DATED : April 22, 2003
INVENTOR(S) : Linker et al.

It is certified that error appears in the above-identified patent and that said Letters Patent is hereby corrected as shown below:

Title page,
Item [*], Notice: should read -- Subject to any disclaimer, the term of this patent Is extended or adjusted under 35 U.S.C. 154(b) By 36 days.

Signed and Sealed this

Sixth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,551,963 B1　　　　　　　　　　　　　　　　　　　　　　　Page 1 of 1
DATED : April 22, 2003
INVENTOR(S) : Linker et al.

It is certified that error appears in the above-identified patent and that said Letters Patent is hereby corrected as shown below:

<u>Title page,</u>
Item [*] Notice, should read
-- [*] Notice:　　This patent issued on a continued prosecution application filed under 37 CFR 1.53(d), and is subject to the twenty year patent term provisions of 35 U.S.C. 154(a)(2)

Subject to any disclaimer, the term of this patent is extended or adjusted under 35 U.S.C.
154(b) by 36 days. --

Signed and Sealed this

Twenty-eighth Day of September, 2004

JON W. DUDAS
*Director of the United States Patent and Trademark Office*